(12) United States Patent
Han et al.

(10) Patent No.: US 12,213,421 B2
(45) Date of Patent: Feb. 4, 2025

(54) NUCLEIC ACID SEQUENCE FOR DETECTING SOYBEAN PLANT DBN8002 AND DETECTION METHOD THEREFOR

(71) Applicant: Beijing Dabeinong Biotechnology Co., Ltd., Haidian District (CN)

(72) Inventors: Chao Han, Beijing (CN); Caihong Yu, Beijing (CN); Xiangting Xie, Beijing (CN); Dengyuan Wang, Beijing (CN); Shujing Yang, Beijing (CN); Guangdong Cui, Beijing (CN); Yuejing Kang, Beijing (CN); Xiaoming Bao, Beijing (CN)

(73) Assignee: Beijing Dabeinong Biotechnology Co. Ltd., Beijing (CN)

( * ) Notice: Subject to any disclaimer, the term of this patent is extended or adjusted under 35 U.S.C. 154(b) by 196 days.

(21) Appl. No.: 17/622,622

(22) PCT Filed: Aug. 9, 2019

(86) PCT No.: PCT/CN2019/099994
§ 371 (c)(1),
(2) Date: Dec. 23, 2021

(87) PCT Pub. No.: WO2021/026688
PCT Pub. Date: Feb. 18, 2021

(65) Prior Publication Data
US 2023/0210075 A1   Jul. 6, 2023

(51) Int. Cl.
*A01H 5/10* (2018.01)
*A01H 6/54* (2018.01)

(52) U.S. Cl.
CPC ............... *A01H 5/10* (2013.01); *A01H 6/542* (2018.05)

(58) Field of Classification Search
CPC .................................................. A01H 6/542
See application file for complete search history.

(56) References Cited

U.S. PATENT DOCUMENTS

| | | | | |
|---|---|---|---|---|
| 5,695,940 A | * | 12/1997 | Drmanac | C12Q 1/6874 536/23.1 |
| 6,137,033 A | * | 10/2000 | Estruch | C07K 14/415 536/23.7 |
| 11,359,210 B2 | | 6/2022 | Price | |

FOREIGN PATENT DOCUMENTS

| | | |
|---|---|---|
| CN | 103719136 | 4/2014 |
| CN | 105567682 | 5/2016 |
| CN | 106119245 | 11/2016 |
| CN | 110903361 | 8/2021 |
| WO | WO-2008106785 A1 * | 9/2008 ........... C12Q 1/6886 |
| WO | 2014004458 | 1/2014 |
| WO | 2014201235 | 12/2014 |
| WO | 2017215327 | 12/2017 |
| WO | 2017215328 | 12/2017 |

OTHER PUBLICATIONS

*Arabidopsis thaliana* genome assembly, chromosome_3—Nucleotide—NCBI, https://www.ncbi.nlm.nih.gov/nucleotide/LR215054.1?report=genbank&log$=nuclalign&blast_rank=9&RID=KWWMR0M7013; Accessed Oct. 29, 2023. (Year: 2023).*
Binary vector pDIVA, complete sequence—Nucleotide—NCBI,https://www.ncbi.nlm.nih.gov/nucleotide/KX665539.1?report=genbank&log$=nuclalign&blast_rank=2&RID=KWX3ETGN016; Accessed Oct. 29, 2023. (Year: 2023).*
Sahu et al. , 2023, Chromosome-scale genomes of commercially important mahoganies, Swietenia macrophylla and Khaya senegalensis. Scientific Data, 10(1), 832. (Year: 2023).*
Liu et a., Jan. 25, 2019, Genomic data of Nanmaohu Park Swietenia macrophylla plant specimen, RL0275 GigaScience Database. http://dx.doi.org/10.5524/101338 (Accessed from http://gigadb.org/dataset/101338, Mar. 6, 2024) (see PDF enclosed). (Year: 2019).*
Swietenia macrophylla isolate HCNGB_00002344 chromosome 27; GenBank: CP135578.1 locus CP135578. (Year: 2023).*
Grishin, Impact of Annealing Temperature and Sequence for Primers of RAPD and ISSR on the Results PCR Analysis DNA of Lupinus Angustifolius, N/A.
Glycine max DNA, BAC clone: GMJENa0191G18_F, 5'end, cultivar: ENREI, European Nucleotide Archive, Jan. 2, 2014, LB119451.1.
Abg56f10.x1 Soybean random, unfiltered genomic library Glycine max genomic, genomic survey sequence, European Nucleotide Archive, Feb. 4, 2014, CL899974.1.
Genbank KX665539, Binary vector pDIVA, complete sequence, 2017.
Sahin, Characterization of Bacillus thuringiensis isolates by their insecticidal activity and their production of Cry and Vip3 proteins, Plos One 13, Nov. 1, 2018, pp. 1-18.

* cited by examiner

*Primary Examiner* — David H Kruse
*Assistant Examiner* — Santosh Sharma
(74) *Attorney, Agent, or Firm* — Marcus C. Dawes

(57) ABSTRACT

The present invention relates to nucleic acid sequences for detecting soybean plant DBN8002 and detection methods thereof, wherein said nucleic acid sequences comprise SEQ ID NO: 1 or a complementary sequence thereof, and/or SEQ ID NO: 2 or a complementary sequence thereof. The soybean plant DBN8002 of the present invention has good resistance against *Lepidoptera* insects as well as good tolerance to glufosinate herbicide without compromising the yield, and the detection methods can accurately and rapidly identify whether a biological sample contains the DNA molecule of the transgenic soybean event DBN8002.

3 Claims, 5 Drawing Sheets
Specification includes a Sequence Listing.

Soybean plant DBN8002　　　　　　　　NGM

Soybean plant DBN8002　　　　　　　　NGM

Soybean plant DBN8002　　　　　　　　NGM

Soybean plant DBN8002 NGM

Soybean plant DBN8002

NGM

Soybean plant DBN8002

NGM

Soybean plant DBN8002

NGM

NUCLEIC ACID SEQUENCE FOR DETECTING SOYBEAN PLANT DBN8002 AND DETECTION METHOD THEREFOR

SEQUENCE LISTING

An ASCII text file entitled "Amended_sequence_listing.txt" has been prepared and the material therein is incorporated by reference in its entirety. The amended ASCII text file was created on Aug. 31, 2022 and is 20.6 KB in size.

FIELD OF THE INVENTION

The present invention relates to the field of plant molecular biology, especially the field of transgenic crop breeding in the agricultural biotechnology research. In particular, the present invention relates to an insect resistant and glufosinate herbicide tolerant transgenic soybean event DBN8002, and nucleic acid sequences for detecting whether a biological sample contains the specific transgenic soybean event DBN8002 and detection methods thereof.

BACKGROUND

Soybean (*Glycine max*) is one of the world's five main crops. Biotechnology has been applied to soybean for improvement of the agronomic traits and the quality thereof. Herbicide tolerance, particularly the tolerance to a glyphosate herbicide, is an important agronomic trait in soybean production. For example, there are successful soybean events such as GTS40-3-2 and MON89788, which have been widely grown in the major soybean planting areas such as the U.S. Another important agronomic trait is insect resistance, especially resistance to *Lepidoptera* insects. For example, there are successful soybean events such as MON87701, which have been widely grown in the major soybean planting areas such as Brazil. It is worth mentioning that Vip proteins have a different action mechanism from Cry proteins, as they are insecticidal proteins during vegetative period and can be used as a means for effectively managing Cry protein resistant insects. The *Lepidoptera* resistance of soybean may be conferred by the expression of *Lepidoptera* resistant genes in soybean plants through a transgenic method. Moreover, glufosinate herbicide has a different action mechanism from glyphosate herbicide, as glufosinate herbicide is a non-selective contact-type herbicide and can be used as a means for effectively managing glyphosate resistant weeds. The glufosinate herbicide tolerance of soybean may be conferred by the expression of glufosinate herbicide tolerant genes (e.g., PAT) in soybean plants through a transgenic method.

It is of great significance to design an expression vector containing functional foreign genes (Vip3Aa and PAT genes) suitable for transforming soybean crops and to obtain the corresponding commercial transgenic soybean events. To date, successful application case of Vip proteins to control insects in soybean plants is not available yet, while herbicide tolerance as an important agronomic trait in soybean production is almost indispensable. Thus, good commercially suitable soybean transformation event requires a comprehensive consideration of the factors such as vector design for the Vip3Aa and PAT genes in soybean plants, interactions between the two expression cassettes, insect resistance efficacy, herbicide tolerance efficacy, and the effects on yield and other plant physiological indices, so that the Vip3Aa and PAT genes can be expressed in appropriate amounts in soybean and serve their corresponding functions without influencing yield and other physiological indices of the soybean event.

The expression of exogenous genes in plants is known to be influenced by their positions on chromosomes, perhaps due to chromatin structure (e.g., heterochromatin) or the proximity of transcriptional regulation elements (e.g., enhancer) to the integration site. For this reason, it is often necessary to screen a large number of events in order to identify the event that can be commercialized (i.e. the event in which an introduced target gene is optimally expressed). For example, it has been observed in plants and other organisms that there may be great difference among events in term of the expression level of an introduced gene; and there may also be differences in term of spatial or temporal patterns of expression, for example, differences in the relative expression of a transgene in various plant tissues, which are reflected in the possible discrepancy between the actual expression pattern and the expected expression pattern based on transcriptional regulatory elements in the introduced gene construct. For this reason, it usually needs to produce hundreds to thousands of different events and screen those events for a single event that has expected transgene expression level and pattern for commercial purposes. An event that has expected expression levels or patterns of a transgene is useful for introgression of the transgene into other genetic backgrounds by sexual outcrossing using conventional breeding methods. The progeny reproduced by such crossing maintains the transgene expression characteristics of the original transformant. This strategy is used to ensure reliable gene expression in a number of varieties that are well adapted to local growing conditions.

It would be advantageous to be able to detect the presence of a particular event in order to determine whether the progeny of a sexual cross contains a target gene. In addition, the method for detecting a particular event would be helpful for complying with the related regulations such as the regulations requiring premarket approval and labeling of the foods derived from recombinant crop plants. It is possible to detect the presence of a transgene by any well-known methods for detecting a polynucleotide, such as polymerase chain reaction (PCR) or DNA hybridization using polynucleotide probes. These detection methods generally focus on frequently used genetic elements, such as promoters, terminators, marker genes. As a result, such methods may not be useful for distinguishing different events, particularly those produced by using the same DNA construct, unless the sequence of the chromosomal DNA adjacent to the inserted transgenic DNA ("flanking DNA") is known. Thus, a pair of primers spanning the junction between the inserted transgene and the flanking DNA is usually used to identify a particular transgenic event by PCR, in particular, a first primer comprised in the inserted sequence and a second primer comprised in the inserted sequence.

SUMMARY OF THE INVENTION

The object of the present invention is to provide nucleic acid sequences for detecting soybean plant DBN8002 and detection methods thereof. The transgenic soybean event DBN8002 has good insect resistance as well as good glufosinate herbicide tolerance. The detection methods can accurately and rapidly identify whether a biological sample contains a DNA molecule of the transgenic soybean event DBN8002.

To achieve the above object, the present invention provides a nucleic acid sequence comprising at least 11 consecutive nucleotides at positions 1-642 of SEQ ID NO: 3 or a complementary sequence thereof, and at least 11 consecutive nucleotides at positions 643-1524 of SEQ ID NO: 3 or a complementary sequence thereof; and/or at least 11 consecutive nucleotides at positions 1-347 of SEQ ID NO: 4 or a complementary sequence thereof, and at least 11 consecutive nucleotides at positions 348-656 of SEQ ID NO: 4 or a complementary sequence thereof.

Preferably, the nucleic acid sequence comprises 22-25 consecutive nucleotides at positions 1-642 of SEQ ID NO: 3 or a complementary sequence thereof, and 22-25 consecutive nucleotides at positions 643-1524 of SEQ ID NO: 3 or a complementary sequence thereof; and/or 22-25 consecutive nucleotides at positions 1-347 of SEQ ID NO: 4 or a complementary sequence thereof, and 22-25 consecutive nucleotides at positions 348-656 of SEQ ID NO: 4 or a complementary sequence thereof.

Preferably, the nucleic acid sequence comprises SEQ ID NO: 1 or a complementary sequence thereof, and/or SEQ ID NO: 2 or a complementary sequence thereof.

Said SEQ ID NO: 1 or a complementary sequence thereof is a sequence of 22 nucleotides that is located around the insertion junction at the 5' end of the inserted sequence in the transgenic soybean event DBN8002. Said SEQ ID NO: 1 or a complementary sequence thereof spans the genomic DNA sequence flanking the soybean insertion site and the DNA sequence at the 5' end of the inserted sequence. Therefore, inclusion of SEQ ID NO: 1 or a complementary sequence thereof could be identified as the presence of the transgenic soybean event DBN8002. Said SEQ ID NO: 2 or a complementary sequence thereof is a sequence of 22 nucleotides that is located around the insertion junction at the 3' end of the inserted sequence in the transgenic soybean event DBN8002. Said SEQ ID NO: 2 or a complementary sequence thereof spans the DNA sequence at the 3' end of the inserted sequence and the genomic DNA sequence flanking the soybean insertion site. Therefore, inclusion of SEQ ID NO: 2 or a complementary sequence thereof could be identified as the presence of the transgenic soybean event DBN8002.

Preferably, the nucleic acid sequence comprises SEQ ID NO: 3 or a complementary sequence thereof, and/or SEQ ID NO: 4 or a complementary sequence thereof.

The nucleic acid sequence of the present invention can be a sequence of at least 11 or more consecutive polynucleotides in any portion of the T-DNA inserted sequence in SEQ ID NO: 3 or a complementary sequence thereof (the first nucleic acid sequence), or at least 11 or more consecutive polynucleotides in any portion of the 5' flanking soybean genomic DNA region in SEQ ID NO: 3 or a complementary sequence thereof (the second nucleic acid sequence). Further, the nucleic acid sequence can be a sequence homologous or complementary to a portion of SEQ ID NO: 3 comprising the entire SEQ ID NO: 1. When used together, the first nucleic acid sequence and the second nucleic acid sequence can act as a DNA primer pair in a DNA amplification method that produces an amplification product. If the amplification product produced by using said DNA primer pair in the DNA amplification method comprises SEQ ID NO: 1, the presence of the transgenic soybean event DBN8002 or progeny thereof can be diagnosed. SEQ ID NO: 3 or a complementary sequence thereof is a sequence of 1524 nucleotides that is located around the insertion junction at the 5' end of the T-DNA inserted sequence in the transgenic soybean event DBN8002. SEQ ID NO: 3 or a complementary sequence thereof consists of 642 nucleotides from the soybean genomic 5' flanking sequence (nucleotides 1-642 of SEQ ID NO: 3), 384 nucleotides from pDBN4006 construct DNA sequence (nucleotides 643-1026 of SEQ ID NO: 3), and 498 nucleotides from prAtAct2 transcription origin sequence (nucleotides 1027-1524 of SEQ ID NO: 3). Therefore, inclusion of SEQ ID NO: 3 or a complementary sequence thereof could be identified as the presence of the transgenic soybean event DBN8002.

The nucleic acid sequence can be a sequence of at least 11 or more consecutive polynucleotides in any portion of the T-DNA inserted sequence in SEQ ID NO: 4 or a complementary sequence thereof (the third nucleic acid sequence), or at least 11 or more consecutive polynucleotides in any portion of the 3' flanking soybean genomic DNA region in SEQ ID NO: 4 or a complementary sequence thereof (the fourth nucleic acid sequence). Further, the nucleic acid sequence can be a sequence homologous or complementary to a portion of SEQ ID NO: 4 comprising the entire SEQ ID NO: 2. When used together, the third nucleic acid sequence and the fourth nucleic acid sequence can act as a DNA primer pair in a DNA amplification method that produces an amplification product. If the amplification product produced by using said DNA primer pair in the DNA amplification method comprises SEQ ID NO: 2, the presence of the transgenic soybean event DBN8002 or progeny thereof can be diagnosed. SEQ ID NO: 4 or a complementary sequence thereof is a sequence of 656 nucleotides that is located around the insertion junction at the 3' end of the T-DNA inserted sequence in the transgenic soybean event DBN8002. SEQ ID NO: 4 or a complementary sequence thereof consists of 145 nucleotides from the DNA sequence of a t35S transcriptional terminator (nucleotides 1-145 of SEQ ID NO:4), 202 nucleotides from pDBN4006 construct DNA sequence (nucleotides 146-347 of SEQ ID NO: 4), and 309 nucleotides from the soybean genomic 3' flanking sequence (nucleotides 348-656 of SEQ ID NO: 4). Therefore, inclusion of SEQ ID NO: 4 or a complementary sequence thereof could be identified as the presence of the transgenic soybean event DBN8002.

Further, the nucleic acid sequence comprises SEQ ID NO: 5 or a complementary sequence thereof.

Said SEQ ID NO: 5 or a complementary sequence thereof is a sequence of 7344 nucleotides that characterizes the transgenic soybean event DBN8002. The specific genomes and genetic elements contained in SEQ ID NO: 5 are shown in Table 1. Inclusion of SEQ ID NO: 5 or a complementary sequence thereof could be identified as the presence of the transgenic soybean event DBN8002.

TABLE 1

The genomes and genetic elements contained in SEQ ID NO: 5.

| Genetic element/genome | Length (bp) | Position in SEQ ID NO: 5 |
| --- | --- | --- |
| 5' genome | 647 | 1-647 |
| RB | 137 | 648-784 |
| prAtAct2 | 1048 | 1032-2439 |
| mVip3Aa | 2370 | 2446-4815 |
| tNos | 253 | 4822-5074 |
| pr35S | 530 | 5128-5657 |
| cPAT | 552 | 5677-6228 |
| t35S | 195 | 6250-6444 |
| LB | 48 | 6599-6646 |
| 3' genome | 698 | 6647-7344 |

As is well known to those skilled in the art, the first, second, third and fourth nucleic acid sequences may not consist of DNA alone, but may also comprise RNA, a mixture of DNA and RNA, or a combination of DNA, RNA and other nucleotides or analogues thereof that do not act as templates for one or more polymerases. In addition, the probes or primers of the present invention should be at least about 11, 12, 13, 14, 15, 16, 17, 18, 19, 20, 21 or 22 consecutive nucleotides in length and may be selected from the nucleotides as set forth in SEQ ID NO: 1, SEQ ID NO: 2, SEQ ID NO: 3, SEQ ID NO: 4 and SEQ ID NO: 5. When selected from the nucleotides as set forth in SEQ ID NO: 3, SEQ ID NO: 4 and SEQ ID NO: 5, the probes and primers may be at least about 21 to about 50 or more consecutive nucleotides in length.

The nucleic acid sequences or complementary sequences thereof can be used in DNA amplification methods to produce amplicons which is used to detect the presence of the transgenic soybean event DBN8002 or progeny thereof in a biological sample. The nucleic acid sequences or complementary sequences thereof can be used in nucleotide detection methods to detect the presence of the transgenic soybean event DBN8002 or progeny thereof in a biological sample.

To achieve the above object, the present invention also provides a method for detecting the presence corresponding to the DNA of the transgenic soybean event DBN8002 in a sample, comprising:
    contacting the sample to be detected with at least two primers for amplifying a target amplification product in a nucleic acid amplification reaction;
    performing the nucleic acid amplification reaction; and
    detecting the presence of the target amplification product;
wherein the target amplification product comprises the nucleic acid sequence.

Preferably, the target amplification product comprises SEQ ID NO: 1 or a complementary sequence thereof, SEQ ID NO: 2 or a complementary sequence thereof, SEQ ID NO: 6 or a complementary sequence thereof, and/or SEQ ID NO: 7 or a complementary sequence thereof.

In particular, the primers comprise a first primer and a second primer, wherein the first primer is selected from SEQ ID NO: 1, SEQ ID NO: 8 and SEQ ID NO: 10; and the second primer is selected from SEQ ID NO: 2, SEQ ID NO: 9 and SEQ ID NO: 11.

To achieve the above object, the present invention also provides a method for detecting the presence of the DNA corresponding to the transgenic soybean event DBN8002 in a sample, comprising:
    contacting the sample to be detected with a probe, wherein the probe comprises the nucleic acid sequence;
    hybridizing the sample to be detected with the probe under stringent hybridization conditions; and
    detecting the hybridization of the sample to be detected with the probe.

The stringent conditions may be hybridization at 65° C. in a solution of 6×SSC (sodium citrate) and 0.5% SDS (sodium dodecyl sulfate), followed by membrane washing in a solution of 2×SSC and 0.1% SDS and a solution of 1×SSC and 0.1% SDS (each for one time).

Preferably, the probe comprises SEQ ID NO: 1 or a complementary sequence thereof, SEQ ID NO: 2 or a complementary sequence thereof, SEQ ID NO: 6 or a complementary sequence thereof, and/or SEQ ID NO: 7 or a complementary sequence thereof. Optionally, at least one of the probes is labeled with at least one fluorophore.

To achieve the above object, the present invention also provides a method for detecting the presence of the DNA corresponding to the transgenic soybean event DBN8002 in a sample, comprising:

contacting the sample to be detected with a marker nucleic acid molecule, wherein the marker nucleic acid molecule comprises the nucleic acid sequence;
    hybridizing the sample to be detected with the marker nucleic acid molecule under stringent hybridization conditions;
    detecting the hybridization of the sample to be detected with the marker nucleic acid molecule, and further performing a marker-assisted breeding analysis for determining whether the insect resistance and/or herbicide tolerance is genetically linked to the marker nucleic acid molecule.

Preferably, the marker nucleic acid molecule comprises at least one sequence selected from the group consisting of SEQ ID NO: 1 or a complementary sequence thereof, SEQ ID NO: 2 or a complementary sequence thereof, and/or SEQ ID NOs: 6-11 or complementary sequences thereof.

To achieve the above object, the present invention also provides a DNA detection kit comprising at least one DNA molecule, wherein the DNA molecule comprises the nucleic acid sequence, and the DNA molecule can act as a DNA primer or a probe specific for the transgenic soybean event DBN8002 or progeny thereof.

Preferably, the DNA molecule comprises SEQ ID NO: 1 or a complementary sequence thereof, SEQ ID NO: 2 or a complementary sequence thereof, SEQ ID NO: 6 or a complementary sequence thereof, and/or SEQ ID NO: 7 or a complementary sequence thereof.

To achieve the above object, the present invention also provides a plant cell comprising a nucleic acid sequence encoding the insect resistant Vip3Aa protein, a nucleic acid sequence encoding the glufosinate herbicide tolerant PAT protein and a nucleic acid sequence of a specific region, wherein the nucleic acid sequence of the specific region comprises the sequence as set forth in SEQ ID NO: 1, SEQ ID NO: 2, SEQ ID NO: 6, and/or SEQ ID NO: 7.

Preferably, the plant cell comprises a nucleic acid sequence encoding the insect resistant Vip3Aa protein, a nucleic acid sequence encoding the glufosinate herbicide tolerant PAT protein and a nucleic acid sequence of a specific region, wherein the nucleic acid sequence of the specific region comprises the sequence as set forth in SEQ ID NO: 3 and/or SEQ ID NO: 4.

Preferably, the plant cell successively comprises SEQ ID NO: 1, the nucleic acid sequence at positions 1032-6444 of SEQ ID NO: 5 and SEQ ID NO: 2, or comprises the sequence as set forth in SEQ ID NO: 5.

To achieve the above object, the present invention also provides a method for protecting a soybean plant from insect invasion, comprising providing at least one transgenic soybean plant cell in the diet of the target insect, wherein the transgenic soybean plant cell comprises in its genome the sequence as set forth in SEQ ID NO: 1 and/or SEQ ID NO: 2; and ingestion of the transgenic soybean plant cell inhibits the target insect from further feeding on the transgenic soybean plant.

Preferably, the transgenic soybean plant cell comprises in its genome the sequence as set forth in SEQ ID NO: 3 and/or SEQ ID NO: 4.

Preferably, the transgenic soybean plant cell successively comprises in its genome SEQ ID NO: 1, the nucleic acid sequence at positions 1032-6444 of SEQ ID NO: 5 and SEQ ID NO: 2, or comprises SEQ ID NO: 5.

To achieve the above object, the present invention also provides a method for protecting a soybean plant from damage caused by a herbicide or controlling weeds in a field in which a soybean plant is planted, comprising applying an effective amount of glufosinate herbicide into the field in which at least one transgenic soybean plant is planted, wherein the transgenic soybean plant comprises in its genome the sequence as set forth in SEQ ID NO: 1 and/or SEQ ID NO: 2, and the transgenic soybean plant has glufosinate herbicide tolerance.

Preferably, the transgenic soybean plant comprises in its genome the sequence as set forth in SEQ ID NO: 3 and/or SEQ ID NO: 4.

Preferably, the transgenic soybean plant successively comprises in its genome SEQ ID NO: 1, the nucleic acid sequence at positions 1032-6444 of SEQ ID NO: 5 and SEQ ID NO: 2, or comprises the sequence as set forth in SEQ ID NO: 5.

To achieve the above object, the present invention also provides a method for breeding an insect resistant and/or glufosinate herbicide tolerant soybean plant, comprising:

planting at least one soybean seed, wherein the soybean seed comprises in its genome a nucleic acid sequence encoding the insect resistant Vip3Aa protein and/or a nucleic acid sequence encoding the glufosinate herbicide tolerant PAT protein, and a nucleic acid sequence of a specific region, or the soybean seed comprises in its genome the nucleic acid sequence as set forth in SEQ ID NO: 5;

growing the soybean seed into a soybean plant; and invading the soybean plant with a target insect, and/or spraying the soybean plant with an effective amount of glufosinate herbicide, and then harvesting the plant with reduced plant damage as compared with other plants which do not comprise the nucleic acid sequence of the specific region;

wherein the nucleic acid sequence of the specific region is the sequence as set forth in SEQ ID NO: 1 and/or SEQ ID NO: 2; preferably, the nucleic acid sequence of the specific region is the sequence as set forth in SEQ ID NO: 3 and/or SEQ ID NO: 4.

To achieve the above object, the present invention also provides a method for producing an insect resistant and/or glufosinate herbicide tolerant soybean plant, comprising:

introducing a nucleic acid sequence encoding the insect resistant Vip3Aa protein and/or a nucleic acid sequence encoding the glufosinate herbicide tolerant PAT protein, and a nucleic acid sequence of a specific region comprised in the genome of a first soybean plant, or the nucleic acid sequence as set forth in SEQ ID NO: 5 comprised in the genome of a first soybean plant, into a second soybean plant, thereby producing a plurality of progeny plants; and selecting the progeny plants comprising the nucleic acid sequence of the specific region, which are also insect resistant and/or glufosinate herbicide tolerant;

wherein the nucleic acid sequence of the specific region is the sequence as set forth in SEQ ID NO: 1 and/or SEQ ID NO: 2; preferably, the nucleic acid sequence of the specific region is the sequence as set forth in SEQ ID NO: 3 and/or SEQ ID NO: 4.

Preferably, the method comprises sexually crossing the transgenic soybean event DBN8002, with a soybean plant that lacks the insect resistance and/or glufosinate herbicide tolerance trait, thereby producing a plurality of progeny plants;

selecting the progeny plants comprising the nucleic acid sequence of the specific region;

invading the progeny plants with a target insect, and/or treating the progeny plants with glufosinate; and selecting the progeny plants which are insect resistant and/or glufosinate herbicide tolerant.

To achieve the above object, the present invention also provides an agricultural product or commodity derived from the transgenic soybean event DBN8002, wherein the agricultural product or commodity is lecithin, fatty acids, glycerol, sterols, soy flakes, soy flours, soy proteins or their concentrates, soybean oils, soy protein fibers, soy milk clots or bean curd.

In the nucleic acid sequences for detecting soybean plants and detection methods thereof according to the present invention, the following definitions and methods are provided to better define the present invention and to guide those skilled in the art in the implementation of the present invention. Unless otherwise stated, the terms are to be understood according to conventional usage by those skilled in the art.

The term "soybean" refers to *Glycine max* and comprises all plant varieties that can mate with the soybean, including wild soybean species.

The term "comprising", "comprise" or "contain" means "including but not limited to".

The term "plant" includes the whole plants, plant cells, plant organs, plant protoplasts, plant cell tissue cultures from which plants can be regenerated, plant calli, plant clumps, and plant cells that are intact in plants or plant parts, wherein the plant parts can be, for example, embryos, pollen, ovules, seeds, leaves, flowers, branches, fruit, stalks, roots, root tips, or anthers. It is to be understood that within the scope of the present invention, the parts of transgenic plants include but are not limited to plant cells, protoplasts, tissues, calli, embryos, flowers, stems, fruits, leaves and roots. The above-mentioned plant parts are derived from the transgenic plants or progeny thereof which have been previously transformed with the DNA molecules of the present invention and therefore at least partially consist of transgenic cells.

The term "gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found in nature. "Endogenous gene" refers to a native gene at its natural location in the genome of an organism. "Exogenous gene" is a foreign gene currently present in the genome of an organism which does not contain it naturally, and also refers to a gene introduced into a receptor cell via a transgenic procedure. Exogenous genes can comprise native genes or chimeric genes inserted into a non-native organism. "Transgene" is a gene that has been introduced into a genome by a transformation procedure. "Insertion site" or "target site" refers to the site in a plant genome into which a recombinant DNA has been inserted.

"Flanking DNA" can comprise either a genome naturally present in an organism such as a plant, or an exogenous (heterologous) DNA introduced via a transformation procedure, e.g. a fragment associated with a transformation event. Thus, flanking DNA may include a combination of native DNA and exogenous DNA. As used herein, the term "flanking DNA", also called as "flanking region", "flanking sequence", "flanking genomic sequence", or "flanking genomic DNA", refers to a sequence of at least 3, 5, 10, 11, 15, 20, 50, 100, 200, 300, 400, 1000, 1500, 2000, 2500 or 5000 base pairs or greater, which is located either immediate upstream or downstream of the originally inserted exogenous DNA molecule and is adjacent to it. When this flanking region is located downstream, it may also be referred to as "3' flank" or "left border flank", and the like. When this flanking region is located upstream, it may also be referred to as "5' flank" or "right border flank", and the like.

Transformation procedures leading to random integration of an exogenous DNA will result in transformants containing different flanking regions which are specific for each transformant. When a recombinant DNA is introduced into a plant through traditional crossing, its flanking regions will generally not be changed. Transformants will also contain unique junctions between a heterologous insert DNA and a genomic DNA fragment, or between two genomic DNA fragments, or between two heterologous DNA fragments. "Junction" is a point where two specific DNA fragments are linked. For example, a junction exists in the position where an insert DNA is linked to a flanking DNA. A junction point also exists in a transformed organism in which two DNA fragments are linked together in a manner modified from that found in the native organism. "Junction region" or "junction sequence" refers to DNA that comprises a junction point.

The present invention provides a transgenic soybean event called DBN8002 and its progeny. The transgenic soybean event DBN8002 is also referred to as a soybean plant DBN8002, including plants and seeds of the transgenic soybean event DBN8002, together with plant cells or renewable parts thereof, wherein the plant parts of the transgenic soybean event DBN8002 include but are not limited to cells, pollens, ovules, flowers, buds, roots, stems, leaves, pods and products derived from the soybean plant DBN8002 such as soybean cakes, powders and oils, specifically lecithin, fatty acids, glycerol, sterols, edible oils, defatted soy flakes, defatted and baked soy flours, soy milk clots, bean curd, soy protein concentrates, isolated soy proteins, hydrolyzed vegetable proteins, organized soy proteins and soy protein fibers.

The transgenic soybean event DBN8002 of the present invention contains a DNA construct that, when expressed in plant cells, confers the transgenic soybean event DBN8002 resistance to insects and tolerance to glufosinate herbicide. The DNA construct comprises two expression cassettes arranged in tandem. The first expression cassette comprises a suitable promoter for expression in a plant and a suitable polyadenylation signal sequence, wherein the promoter is operably linked to the nucleic acid sequence of Vip3Aa protein, which is mainly resistant to *Lepidoptera* insects. The second expression cassette comprises a suitable promoter for expression in a plant and a suitable polyadenylation signal sequence, wherein the promoter is operably linked to a gene encoding phosphinothricin N-acetyltransferase (PAT), and the nucleic acid sequence of the PAT protein is tolerant to glufosinate herbicide. Furthermore, the promoter may be a suitable promoter isolated from plants, including constitutive, inducible and/or tissue specific promoters. The suitable promoter includes but is not limited to, Cauliflower mosaic virus (CaMV) 35S promoter, figwort mosaic virus (FMV) 35S promoter, Ubiquitin promoter, Actin promoter, *Agrobacterium tumefaciens* nopaline synthetase (NOS) promoter, octopine synthetase (OCS) promoter, Cestrum yellow leaf curl virus promoter, Patatin promoter, ribulose-1,5-bisphosphate carboxylase/oxygenase (RuBisCO) promoter, glutathione S-transferase (GST) promoter, E9 promoter, GOS promoter, alcA/alcR promoter, *Agrobacterium rhizogenes* RolD promoter and *Arabidopsis thaliana* Suc2 promoter. The polyadenylation signal sequence may be a suitable polyadenylation signal sequence that works in plants. The suitable polyadenylation signal sequence includes but is not limited to, a polyadenylation signal sequence derived from nopaline synthetase (NOS) gene of *Agrobacterium tumefaciens*, a polyadenylation signal sequence derived from Cauliflower mosaic virus (CaMV) 35S terminator, a polyadenylation signal sequence derived from Protease Inhibitor II (PIN II) gene and a polyadenylation signal sequence derived from α-tubulin gene.

Moreover, the expression cassette may further comprise other genetic elements, including but not limited to an enhancer and a signal peptide/transit peptide. The enhancer, enhancing gene expression level, includes but is not limited to Tobacco Etch Virus (TEV) translation activator, CaMV35S enhancer and FMV35S enhancer. The signal peptide/transit peptide may direct Vip3Aa protein and/or PAT protein for transporting to extracellular space or into a specific intracellular organelle or compartment. For example, a sequence encoding chloroplast transit peptide is used for targeting chloroplast, or a 'KDEL' retention sequence is used for targeting endoplasmic reticulum.

Said mVip3Aa gene may be isolated from *Bacillus thuringiensis* (Abbr. as Bt), and the nucleotide sequence of mVip3Aa gene can be changed through codon optimization or other methods, so as to improve the stability and availability of a transcript in the transformed cells.

The term "*Lepidoptera*", including both moths and butterflies, is the largest order of pests in agriculture and forestry. It includes for example *Agrotis ipsilon* (Rottemberg), *Helicoverpa armigera* (Hubner), *Prodenia litura, Athetis lepigone*, and *Conogethes punctiferalis*.

The phosphinothricin N-acetyltransferase (PAT) gene can be an enzyme isolated from *Streptomyces viridochromogenes* strain, which catalyzes the conversion of L-phosphinothricin into its inactive form by acetylation so as to confer glufosinate herbicide tolerance to the plant. Phosphinothricin (PTC, 2-amino-4-methylphosphinyl-butyric acid) is an inhibitor of glutamine synthetase. PTC is a structural unit of the antibiotic 2-amino-4-methylphosphinyl-alanyl-alanine. This tripeptide (PTT) is active against Gram-positive and Gram-negative bacteria and fungus, *Botrytis cinerea*. The phosphinothricin N-acetyltransferase (PAT) gene may also serve as a selective marker gene.

The "glufosinate" (also known as phosphinothricin) refers to ammonium-2-amino-4-[hydroxy(methyl)phosphinyl]butyrate. Treatments with a "glufosinate herbicide" refer to treatments with any herbicide formulation containing glufosinate. It is within the skills of the ordinary agricultural technician to select application rates for a glufosinate formulation so as to realize a biologically effective amount. Treatment of a field containing plant materials from the transgenic soybean event DBN8002 with any herbicide formulation containing glufosinate will control the growth of weeds in the field and will not affect the growth or yield of the plant materials derived from the transgenic soybean event DBN8002.

The DNA construct is introduced into a plant via transformation methods including but not limited to *Agrobacterium*-mediated transformation, ballistic transformation and pollen tube pathway transformation.

The *Agrobacterium*-mediated transformation is a commonly-used method for plant transformation. The exogenous DNA to be introduced into a plant is cloned into a vector between left and right border consensus sequences, i.e., a T-DNA region. The vector is transformed into *Agrobacterium* cells, which are subsequently used to infect plant tissues. The T-DNA region in the vector comprising the exogenous DNA is inserted into the plant genome.

Ballistic transformation is bombardment of plant cells with a vector comprising the exogenous DNA (particle-mediated biolistic transformation).

The pollen tube pathway transformation is a method for carrying the exogenous DNA into an embryo sac via a nucellus pathway using a natural pollen tube (also known as the transmitting tissue of pollen tube) formed after plant pollination.

After transformation, it is necessary to regenerate the transgenic plant from the transformed plant tissue, and select the progeny with the exogenous DNA using a suitable marker.

A DNA construct is an assembly of DNA molecules linked together that provides one or more expression cassettes. The DNA construct is preferably a plasmid that can self-replicate in a bacterial cell and contains various restriction endonuclease sites that are useful for introducing DNA molecules that provide functional genetic elements, i.e. promoters, introns, leader sequences, coding sequences, 3' terminator regions and other sequences. The expression cassettes contained in a DNA construct comprise genetic elements which are necessary for the transcription of a messenger RNA and can be designed to express in prokaryote cells or eukaryotic cells. Most preferably, the expression cassettes of the present invention are designed to express in plant cells.

A transgenic "event" is produced by transformation of plant cells with a heterologous DNA construct, including the steps of inserting a nucleic acid expression cassette comprising at least one target gene into the genome of a plant through a transgenic method in order to generate a plant population, regenerating the plant population, and selecting a particular plant having the characteristics of insertion into a particular genome location. The term "event" refers to the original transformant and progeny thereof that include a heterologous DNA. The term "event" also refers to progeny produced by sexually crossing the original transformant with an individual of other varieties that include the heterologous DNA. Even after repeated back-crossing with a backcross parent, the inserted DNA and flanking genomic DNA from the original transformant parent are still present at the same chromosomal location in the crossing progeny. The term "event" also refers to a DNA sequence from the original transformant comprising an inserted DNA and flanking genomic sequences immediately adjacent to the inserted DNA, wherein the DNA sequence would be expected to be transferred to a progeny that is produced by sexually crossing a parental line that includes the inserted DNA (e.g., the original transformant and progeny thereof resulting from selfing) with a parental line that does not contain the inserted DNA, and receives the inserted DNA including the target gene.

"Recombination" as used herein refers to a form of a DNA and/or a protein and/or an organism that would not normally be found in nature and as such is created by human intervention. Such human intervention may produce a recombinant DNA molecule and/or a recombinant plant. The "recombinant DNA molecule" is obtained by an artificial combination of two otherwise separated sequence segments, e.g., by chemical synthesis or by the manipulation of isolated nucleic acid segments using genetic engineering technology. The technology of operating nucleic acids is well known in the art.

The term "transgene" includes any cell, cell line, callus, tissue, plant part or plant, the genotype of which has been changed due to the presence of a heterologous nucleic acid. "Transgene" includes those transgenic organisms initially so altered as well as the individual progeny produced from the original transgenic organism by sexual cross or asexual propagation. The term "transgene" as used herein does not encompass the (chromosomal or extrachromosomal) alteration of genome by conventional plant breeding methods or by naturally occurring events, such as random cross-fertilization, non-recombinant viral infection, non-recombinant bacterial transformation, non-recombinant transposition or spontaneous mutation.

"Heterologous" as used herein refers to a first molecule which is not normally found in combination with a second molecule in nature. For example, a molecule may be derived from a first species and inserted into the genome of a second species. The molecule would thus be heterologous to the host and artificially introduced into the genome of the host cell.

The transgenic soybean event DBN8002 having *Lepidoptera* insect resistance and glufosinate herbicide tolerance can be bred by the following steps: firstly, sexually crossing a first parental soybean plant consisting of a soybean plant cultured from the transgenic soybean event DBN8002 and progeny thereof, with a second parental soybean plant that lacks *Lepidoptera* insect resistance and glufosinate herbicide tolerance, thereby producing a plurality of first progeny plants, wherein the transgenic soybean event DBN8002 and progeny thereof are obtained from the transformation using the expression cassette of the present invention that is resistant to *Lepidoptera* insects and tolerant to glufosinate herbicide; and then selecting a progeny plant that is resistant to the invasion of *Lepidoptera* insects and/or tolerant to glufosinate herbicide, thereby breeding a soybean plant that is resistant to the invasion of *Lepidoptera* insects and tolerant to glufosinate herbicide. These steps can further include backcrossing the *Lepidoptera* insect resistant and/or glufosinate tolerant progeny plant with the second parental soybean plant or a third parental soybean plant, then screening the progeny by invasion of *Lepidoptera* insects, application of glufosinate herbicide or identification of molecular markers (e.g., the DNA molecule comprising the junctions identified from the 5' and 3' ends of the inserted sequence in the transgenic soybean event DBN8002) associated with the trait, thereby producing a *Lepidoptera* insect resistant and glufosinate herbicide tolerant soybean plant.

It is also to be understood that two different transgenic plants can also be crossed to produce progeny that contains two independent and separately added exogenous genes. Selfing of appropriate progeny can produce progeny plants that are homozygous for both of the added exogenous genes. Backcrossing with a parental plant and outcrossing with a non-transgenic plant as previously described are also contemplated, as is vegetative propagation.

The term "probe" means an isolated nucleic acid molecule which is attached to a conventional detectable label or reporter molecule, for example, a radioactive isotope, a ligand, a chemiluminescent agent, or an enzyme. Such a probe is complementary to a strand of a target nucleic acid, in the present invention, to a DNA strand from the genome of the transgenic soybean event DBN8002 genome, no matter whether the genome DNA is from the transgenic soybean event DBN8002 or seed or from a plant or seed or extract thereof derived from the transgenic soybean event DBN8002. Probes of the present invention include not only deoxyribonucleic acids or ribonucleic acids, but also polyamides and other probe materials that bind specifically to a target DNA sequence and can be used to detect the presence of that target DNA sequence.

The term "primer" is a fragment of isolated nucleic acid molecule that are annealed to a complementary target DNA strand by nucleic acid hybridization to form a hybrid between the primer and the target DNA strand, then extended along the target DNA strand under the action of a polymerase (for example, a DNA polymerase). Primer pairs of the present invention refer to their use in the amplification of a target nucleic acid sequence, for example, by polymerase chain reaction (PCR) or other conventional nucleic acid amplification methods.

Probes and primers are generally 11 polynucleotides or more in length, preferably 18 polynucleotides or more, more preferably 24 polynucleotides or more, most preferably 30 polynucleotides or more. Such probes and primers hybridize specifically to a target sequence under high stringency hybridization conditions. Preferably, probes and primers of the present invention have complete DNA sequence identity with consecutive nucleic acids in a target sequence, though a probe that differs from the target DNA sequence and retains the ability to hybridize to the target DNA sequence under high stringency conditions may be designed by conventional methods.

Primers and probes based on the flanking genomic DNA and the inserted sequence of the present invention can be determined by conventional methods, for example, by isolating the corresponding DNA molecule from a plant material derived from the transgenic soybean event DBN8002, and determining the nucleic acid sequence of the DNA molecule. The DNA molecule comprises the transgenic inserted sequence and soybean genomic flanking sequences, and a fragment of the DNA molecule may be used as a primer or probe.

The nucleic acid probe and primer of the present invention hybridize to a target DNA sequence under stringent conditions. Any conventional nucleic acid hybridization or amplification method can be used to identify the presence of a DNA from the transgenic soybean event DBN8002 in a sample. Nucleic acid molecules or fragments thereof are capable of specifically hybridizing to other nucleic acid molecules under certain circumstances. As used herein, two nucleic acid molecules are capable of specifically hybridizing to each other if the two molecules are capable of forming an anti-parallel, double-stranded nucleic acid structure. A nucleic acid molecule is said to be the "complement" of the other nucleic acid molecule if they exhibit complete complementarity. As used herein, two nucleic acid molecules are said to exhibit "complete complementarity", if every nucleotide of a nucleic acid molecule is complementary to the corresponding nucleotide of the other nucleic acid molecule. Two nucleic acid molecules are said to be "minimally complementary", if they can hybridize to each other with sufficient stability such that they can anneal and bind to each other under at least conventional "low stringency" conditions. Similarly, two nucleic acid molecules are said to possess "complementarity", if they can hybridize to each other with sufficient stability such that they can anneal and bind to each other under conventional "high stringency" conditions. Departures from complete complementarity are permissible, as long as such departures do not completely preclude the two molecules from forming a double-stranded structure. To serve as a primer or probe, a nucleic acid molecule only needs to have sufficient complementarity in sequence such that it can form a stable double-stranded structure under the particular solvent and salt concentrations employed.

As used herein, a substantially homologous sequence is a nucleic acid molecule which will specifically hybridize to a complementary strand of another matching nucleic acid molecule under high stringency conditions. Appropriate stringent conditions which promote DNA hybridization are known to those skilled in the art, for example, treating with 6.0×sodium chloride/sodium citrate (SSC) at about 45° C., followed by washing with 2.0×SSC at 50° C. For example, the salt concentration in the washing step can be about 2.0×SSC at 50° C. in low stringency conditions to about 0.2×SSC at 50° C. in high stringency conditions. In addition, the temperature in the washing step can be increased from room temperature (about 22° C.) in low stringency conditions to about 65° C. in high stringency conditions. Both temperature and salt concentration may be varied, or one of them may be held constant while the other variable is changed. Preferably, a nucleic acid molecule of the present invention will specifically hybridize to one or more nucleic acid molecules of SEQ ID NO: 1, SEQ ID NO: 2, SEQ ID NO: 3, SEQ ID NO: 4, SEQ ID NO: 5, SEQ ID NO: 6 and SEQ ID NO: 7, or complementary sequences thereof, or any fragment of the above sequences under moderate stringency conditions, for example at about 2.0×SSC and about 65° C. More preferably, a nucleic acid molecule of the present invention will specifically hybridize to one or more nucleic acid molecules of SEQ ID NO: 1, SEQ ID NO: 2, SEQ ID NO: 3, SEQ ID NO: 4, SEQ ID NO: 5, SEQ ID NO: 6 and SEQ ID NO: 7, or complementary sequences thereof, or any fragment of the above sequences under high stringency conditions. A preferred marker nucleic acid molecule of the present invention comprises SEQ ID NO: 1, SEQ ID NO: 2, SEQ ID NO: 6 and SEQ ID NO: 7, or complementary sequences thereof, or any fragment of the above sequences. Another preferred marker nucleic acid molecule of the present invention has 80% to 100% or 90% to 100% sequence identity with SEQ ID NO: 1, SEQ ID NO: 2, SEQ ID NO: 6 and SEQ ID NO: 7, or complementary sequences thereof, or any fragment of the above sequences. SEQ ID NO: 1, SEQ ID NO: 2, SEQ ID NO: 6 and SEQ ID NO: 7 may be used as markers in plant breeding methods to identify progeny of genetic cross. The hybridization of a probe to a target DNA molecule can be detected by any method well-known to those skilled in the art, including but not limited to, fluorescent tags, radioactive tags, antibody-based tags, and chemiluminescent tags.

Regarding the amplification of a target nucleic acid sequence using particular amplification primers (for example, PCR), "stringent conditions" are conditions that permit a primer to hybridize only to a target nucleic acid sequence in a DNA thermal amplification reaction, wherein the primer has a wild-type sequence corresponding to the target nucleic acid sequence (or its complementary sequence) and thus could bind to it, preferably to produce a unique amplification product, i.e. amplicon.

The term "binding specifically to (a target sequence)" indicates that under stringent hybridization conditions, a probe or primer hybridizes only to a target sequence in a sample comprising the target sequence.

As used herein, "amplicon" refers to a nucleic acid amplification product of a target nucleic acid sequence used as a part of the nucleic acid template. For example, in order to determine whether a soybean plant is produced by sexually crossing the transgenic soybean event DBN8002 of the present invention, or whether a soybean sample collected from a field comprises the transgenic soybean event DBN8002, or whether a soybean extract (such as a meal, flour or oil) comprises the transgenic soybean event DBN8002, the DNA extracted from a soybean plant tissue sample or extract may be subject to a nucleic acid amplification method using a primer pair to produce an amplicon that is diagnostic for the presence of the DNA of the transgenic soybean event DBN8002. The primer pair includes a first primer derived from the flanking sequences in the plant genome adjacent to the insertion site of the inserted exogenous DNA, and a second primer derived from the inserted exogenous DNA. The amplicon has a length and a sequence that is also diagnostic for the transgenic soybean event DBN8002. The amplicon may have a length equal to the sum of the combined length of the primer pairs plus one nucleotide base pair, or preferably plus about 50 nucleotide base pairs, or more preferably plus about 250 nucleotide base pairs, or most preferably plus about 450 nucleotide base pairs or more.

Alternatively, a primer pair can be derived from flanking genomic sequences on both sides of the inserted DNA so as to produce an amplicon that includes the entire inserted nucleotide sequence. One of the primer pair derived from the plant genomic sequence may be located at a distance from the inserted DNA sequence, and this distance can range from one nucleotide base pair to about twenty thousand nucleotide base pairs. As used herein, the term "amplicon" specifically excludes primer dimers formed in a DNA thermal amplification reaction.

Nucleic acid amplification reaction can be accomplished by any one of various nucleic acid amplification methods known in the art, including polymerase chain reaction (PCR). A variety of nucleic acid amplification methods are known to those skilled in the art. PCR amplification methods have been developed to amplify up to 22 kb genomic DNA and up to 42 kb bacteriophage DNA. These methods as well as other DNA amplification methods known in the art can be used in the present invention. The inserted exogenous DNA sequence and flanking DNA sequences from the transgenic soybean event DBN8002 can be amplified on the genome of the transgenic soybean event DBN8002 using the primer sequences provided. After amplification, the PCR amplicon or cloned DNA is sequenced by standard sequencing methods.

DNA detection kits that are based on DNA amplification methods contain DNA molecules used as primers that hybridize specifically to a target DNA and amplify a diagnostic amplicon under appropriate reaction conditions. The kit may provide an agarose gel-based detection method or many known methods in the art for detecting a diagnostic amplicon. Provided by the present invention is a kit that contains DNA primers that are homologous or complementary to any portion of the soybean genome in SEQ ID NO: 3 or SEQ ID NO: 4 and to any portion of the transgenic inserted region in SEQ ID NO: 5. A primer pair that is specifically identified as useful in a DNA amplification method comprises SEQ ID NO: 8 and SEQ ID NO: 9, which amplify a diagnostic amplicon homologous to a portion of 5' transgene/genome region of the transgenic soybean event DBN8002, wherein the amplicon comprises SEQ ID NO: 1. Other DNA molecules useful as DNA primers can be selected from SEQ ID NO: 5.

The amplicon produced by these methods may be detected by a plurality of techniques. One of such methods is Genetic Bit Analysis, in which a DNA oligonucleotide strand that spans the inserted DNA sequence and the adjacent flanking genomic DNA sequences is designed. The oligonucleotide strand is immobilized in wells of a microwell plate. Following the PCR amplification of the target region (using two primers respectively for the inserted sequence and the adjacent flanking genomic sequence), a single-stranded PCR product can be hybridized to the immobilized oligonucleotide and serve as a template for a single base extension reaction using a DNA polymerase and specifically labeled ddNTPs for the next expected base. The result can be obtained by fluorescent or ELISA-based methods. A signal indicates the presence of the inserted/flanking genomic sequence, which demonstrates that the amplification, hybridization, and single base extension are successful.

Another method is the Pyrosequencing technique. In this method, an oligonucleotide strand that spans the inserted DNA sequence and the adjacent genomic DNA junction part is designed. The oligonucleotide strand is hybridized to the single-stranded PCR product from the target region (using two primers respectively for the inserted sequence and the adjacent flanking genomic sequence) and incubated together with a DNA polymerase, ATP, sulfurylase, luciferase, apyrase, adenosine-5'-phosphosulfate and luciferin. The dNTPs are added separately and the produced light signal is measured. A light signal indicates the presence of the inserted/flanking sequence, which demonstrates that the amplification, hybridization, and single or multi-base extension are successful.

Fluorescence polarization phenomenon as described by Chen et al. (Genome Res., 1999, 9: 492-498) is also a method that can be used to detect the amplicon of the present invention. To use this method, an oligonucleotide strand that spans the inserted DNA sequence and the adjacent genomic DNA junction part needs to be designed. The oligonucleotide strand is hybridized to the single-stranded PCR product from the target region (using two primers respectively for the inserted sequence and the adjacent flanking genomic sequence) and incubated together with a DNA polymerase and a fluorescently labeled ddNTP. Single base extension results in the incorporation of ddNTP. Such incorporation can be measured as a change in polarization using a fluorometer. A change in polarization indicates the presence of the inserted/flanking sequence, which demonstrates that the amplification, hybridization, and single base extension are successful.

Taqman is described as a method for detecting and quantitatively analyzing the presence of a DNA sequence and is fully described in the instructions provided by the manufacturer. Now, it is briefly illustrated as follows. A FRET oligonucleotide probe which spans the inserted DNA sequence and the adjacent genomic flanking junction part is designed. The FRET probe and PCR primers (using two primers respectively for the inserted sequence and the adjacent flanking genomic sequence) are subject to reaction cycles in the presence of a thermostable polymerase and dNTPs. Hybridization of the FRET probe results in cleavage between the fluorescent moiety and quenching moiety on the FRET probe and release of the fluorescent moiety. The generation of a fluorescent signal indicates the presence of the inserted/flanking sequence, which demonstrates that the amplification and hybridization are successful.

Based on the hybridization principle, suitable techniques for detecting plant materials from the transgenic soybean event DBN8002 also comprise Southern blot, Northern blot and in situ hybridization. Particularly, the suitable techniques involve incubating a probe with a sample, washing them to remove unbound probe, and detecting whether the probe has been hybridized. The detection method is dependent on the type of the label attached to the probe, for example, a radioactively labeled probe can be detected by exposure and development of X-ray film, or an enzymatically labeled probe may be detected by conversion of a substrate to effect a color change.

The application of molecular markers in sequence detection has been described by Tyangi et al. (Nature Biotech., 1996, 14: 303-308), which is briefly described as follows. A FRET oligonucleotide probe that spans the inserted DNA sequence and the adjacent genomic flanking junction part is designed. Due to the unique structure of the FRET probe, it contains a secondary structure that keeps the fluorescent moiety and the quenching moiety in close proximity. The FRET probe and PCR primers (using two primers respectively for the inserted sequence and the flanking genomic sequence) are subject to reaction cycles in the presence of a thermostable polymerase and dNTPs. Following successful PCR amplification, hybridization of the FRET probe to the target sequence results in loss of the probe's secondary structure, so that the fluorescent moiety and the quenching moiety are spatially separated and a fluorescent signal is generated. The generation of a fluorescent signal indicates the presence of the inserted/flanking sequence, which demonstrates that the amplification and hybridization are successful.

Other described methods, such as microfluidics, provide methods and devices for isolating and amplifying DNA samples. Optical dyes are used to detect and determine specific DNA molecules. Nanotube devices are useful for detecting the DNA molecules of the present invention, which comprise an electronic sensor for detecting DNA molecules or nanobeads for binding specific DNA molecules and thus can be detected.

DNA detection kits can be developed using the compositions described herein and the methods described or known in the field of DNA detection. The kits are useful for identifying whether a sample contains the DNA of the transgenic soybean event DBN8002 and can be applied to breed soybean plants containing the DNA of the transgenic soybean event DBN8002. The kits may contain DNA primers or probes that are homologous or complementary to at least a portion of SEQ ID NO: 1, 2, 3, 4 or 5, or contain other DNA primers or probes homologous or complementary to the DNA contained in the transgenic genetic elements of DNA, and these DNA sequences can be used in DNA amplification reactions or as probes in DNA hybridization methods. The DNA structure of the transgenic inserted sequence and the soybean genomic junction part contained in the soybean genome and illustrated in FIG. 1 and Table 1 comprises: the soybean DBN8002 flanking genomic region adjacent to the 5' end of the transgenic inserted sequence; a portion of an inserted sequence from the right border region (RB) of *Agrobacterium*; a first expression cassette consisting of an *Arabidopsis* ACTIN2 promoter (prAtAct2), operably linked to the insect resistant mVip3Aa gene of *Bacillus thuringiensis*, further operably linked to a nopaline synthetase terminator (tNos); a second expression cassette consisting of a cauliflower mosaic virus 35S promoter (pr35S), operably linked to a glufosinate tolerant phosphinothricin-N-acetyltransferase gene (cPAT) of *Streptomyces*, further operably linked to a cauliflower mosaic virus 35S terminator (t35S); a portion of an inserted sequence from the left border region (LB) of *Agrobacterium*; and soybean plant DBN8002 flanking genomic region at the 3' end of the transgenic inserted sequence (SEQ ID NO: 5). In DNA amplification methods, the DNA molecules useful as primers can be any portion derived from the transgene inserted sequence in the transgenic soybean event DBN8002, or any portion derived from the flanking soybean genomic DNA sequence in the transgenic soybean event DBN8002.

The transgenic soybean event DBN8002 can be used in combination with other transgenic soybean varieties, for example, herbicide (such as glyphosate and dicamba) tolerant transgenic soybean varieties, or transgenic soybean varieties carrying other insect resistant genes. Various combinations of these different transgenic events, when used to breed with the transgenic soybean event DBN8002 of the present invention, can provide improved hybrid transgenic soybean varieties resistant to various insects and tolerant to various herbicides. These varieties exhibit better performances such as increased yield, as compared with non-transgenic varieties and single-trait transgenic varieties.

The transgenic soybean event DBN8002 of the present invention is resistant to the ingestion damage caused by *Lepidoptera* pests, and tolerant to the phytotoxicity of agricultural herbicides containing glufosinate. The dual-trait soybean plant expresses the Vip3Aa protein of *Bacillus thuringiensis*, providing resistance to the ingestion damage caused by *Lepidoptera* pests (such as *Clanis bilineata*), and expresses glufosinate resistant phosphinothricin-N-acetyltransferase (PAT) protein of *Streptomyces*, conferring glufosinate tolerance to the plant. The dual-trait soybean has the following advantages: 1) economic losses due to *Lepidoptera* pests (such as *Clanis bilineata* and *Prodenia litura*) are avoided, wherein *Clanis bilineata* and *Prodenia litura* are major pests in soybean planting areas; 2) application of agricultural herbicides containing glufosinate confers the soybean an ability for broad-spectrum control of weeds; and 3) soybean production is not reduced. In addition, the transgenes encoding insect resistant and glufosinate tolerant traits are linked on the same DNA segment, and exist in a single locus of the transgenic soybean event DBN8002 genome, which provide an enhanced breeding efficacy and allow to track the transgenic inserted fragments in the propagating population and progeny thereof by using molecular markers. Meanwhile, in the detection methods of the present invention, SEQ ID NO: 1 or a complementary sequence thereof, SEQ ID NO: 2 or a complementary sequence thereof, SEQ ID NO: 6 or a complementary sequence thereof, or SEQ ID NO: 7 or a complementary sequence thereof can be used as DNA primers or probes to produce amplification products diagnostic for the transgenic soybean event DBN8002 or progeny thereof, and rapidly, accurately and stably identify the presence of plant materials from the transgenic soybean event DBN8002.

BRIEF DESCRIPTION OF SEQUENCES

SEQ ID NO: 1 a sequence of 22 nucleotides in length that is located around the insertion junction at the 5' end of the inserted sequence in the transgenic soybean event DBN8002, wherein the nucleotides 1-11 and nucleotides 12-22 are located respectively at either side of the insertion site of soybean genome;

SEQ ID NO: 2 a sequence of 22 nucleotides in length that is located around the insertion junction at the 3' end of the inserted sequence in the transgenic soybean event DBN8002, wherein the nucleotides 1-11 and nucleotides 12-22 are located respectively at either side of the insertion site of soybean genome;

SEQ ID NO: 3 a sequence of 1524 nucleotides that is located around the insertion junction at the 5' end of the inserted sequence in the transgenic soybean event DBN8002;

SEQ ID NO: 4 a sequence of 656 nucleotides that is located around the insertion junction at the 3' end of the inserted sequence in the transgenic soybean event DBN8002;

SEQ ID NO: 5 the entire T-DNA sequence, 5' and 3' end soybean genomic flanking sequences;

SEQ ID NO: 6 a sequence located in SEQ ID NO: 3, spanning the DNA sequence of the pDBN4006 construct and a prAtAct2 transcription origin sequence;

SEQ ID NO: 7 a sequence located in SEQ ID NO: 4, spanning a t35S transcriptional terminator sequence and the DNA sequence of the pDBN4006 construct;

SEQ ID NO: 8 a first primer for amplifying SEQ ID NO: 3;

SEQ ID NO: 9 a second primer for amplifying SEQ ID NO: 3;

SEQ ID NO: 10 a first primer for amplifying SEQ ID NO: 4;

SEQ ID NO: 11 a second primer for amplifying SEQ ID NO: 4;

SEQ ID NO: 12 a primer from 5' flanking genomic sequence;

SEQ ID NO: 13 a primer from T-DNA, which is paired with SEQ ID NO: 12;

SEQ ID NO: 14 a primer from 3' flanking genomic sequence, which can be used in pair with SEQ ID NO: 12 to detect whether a transgene is homozygous or heterozygous;

SEQ ID NO: 15 a primer from T-DNA, which is paired with SEQ ID NO: 14;

SEQ ID NO: 16 a first primer for detecting mVip3Aa gene in Taqman;

SEQ ID NO: 17 a second primer for detecting mVip3Aa gene in Taqman;

SEQ ID NO: 18 a probe for detecting mVip3Aa gene in Taqman;

SEQ ID NO: 19 a first primer for detecting PAT gene in Taqman;

SEQ ID NO: 20 a second primer for detecting PAT gene in Taqman;

SEQ ID NO: 21 a probe for detecting PAT gene in Taqman;

SEQ ID NO: 22 a first primer for soybean endogenous gene lectin;

SEQ ID NO: 23 a second primer for soybean endogenous gene lectin;

SEQ ID NO: 24 a probe for mVip3Aa gene in Southern blot assay;

SEQ ID NO: 25 a probe for PAT gene in Southern blot assay;

SEQ ID NO: 26 a primer from T-DNA, which has the same direction as SEQ ID NO: 13;

SEQ ID NO: 27 a primer from T-DNA, which has an opposite direction to SEQ ID NO: 13 and is used for obtaining a flanking sequence;

SEQ ID NO: 28 a primer from T-DNA, which has an opposite direction to SEQ ID NO: 13 and is used for obtaining a flanking sequence;

SEQ ID NO: 29 a primer from T-DNA, which has the same direction as SEQ ID NO: 15;

SEQ ID NO: 30 a primer from T-DNA, which has an opposite direction to SEQ ID NO: 15 and is used for obtaining a flanking sequence;

SEQ ID NO: 31 a primer from T-DNA, which has an opposite direction to SEQ ID NO: 15 and is used for obtaining a flanking sequence.

The technical solutions of the present invention will be further described below in detail with reference to the accompanying figures and examples.

PARTICULAR EMBODIMENTS OF THE INVENTION

Technical solutions of the nucleic acid sequences for detecting the soybean plant DBN8002 and detection methods thereof according to the present invention will be further illustrated below with reference to the specific examples.

Example 1: Cloning and Transformation

1.1 Vector Cloning

Figure 1:
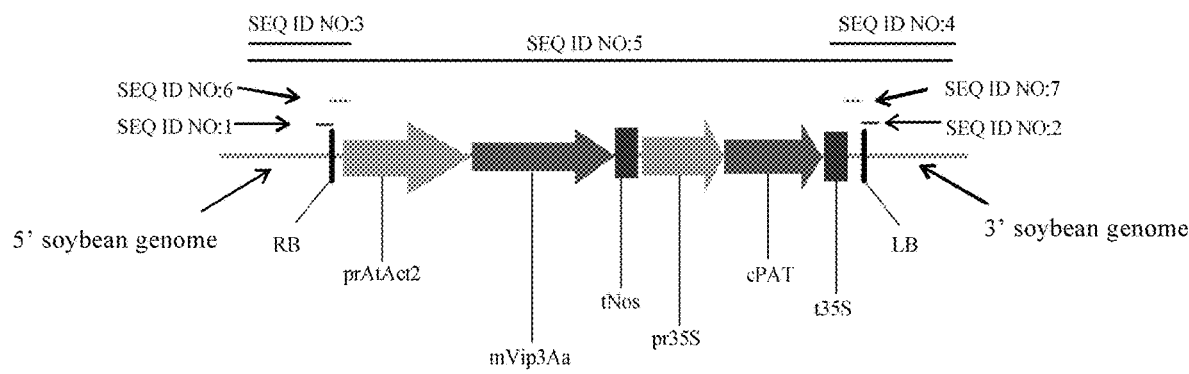
FIG. 1 is a structural scheme of the junction sites between the transgenic inserted sequences and the soybean genome, and a scheme of relative positions of nucleic acid sequences for detecting soybean plant DBN8002 (for the scheme of relative positions, please refer to Wm82.a2 RefGen) in the nucleic acid sequences for detecting soybean plants DBN8002 and detection methods thereof according to the present invention.
Figure 2:
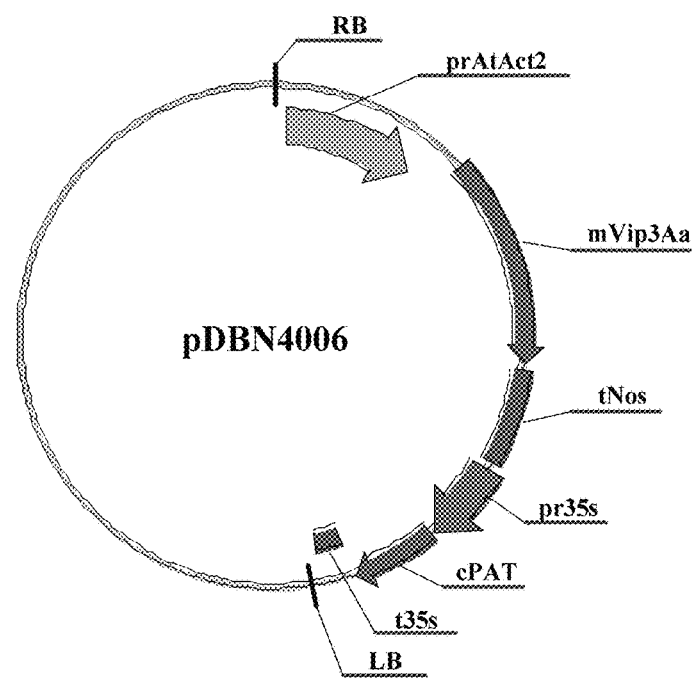
FIG. 2 is a structural scheme of the recombinant expression vector pDBN4006 in the nucleic acid sequences for detecting the soybean plant DBN8002 and detection methods thereof according to the present invention.
Figure 3:
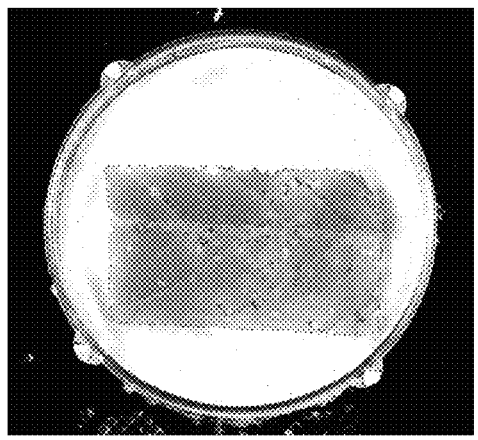
FIG. 3 shows the bioassay effect of the transgenic soybean event DBN8002 against *Helicoverpa armigera* (Hubner) in the nucleic acid sequences for detecting the soybean plant DBN8002 and detection methods thereof according to the present invention.
Figure 3:
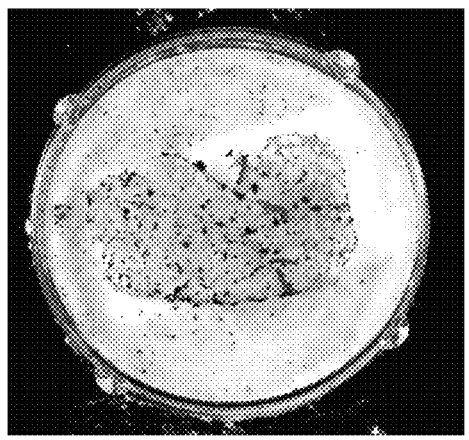
Figure 4:
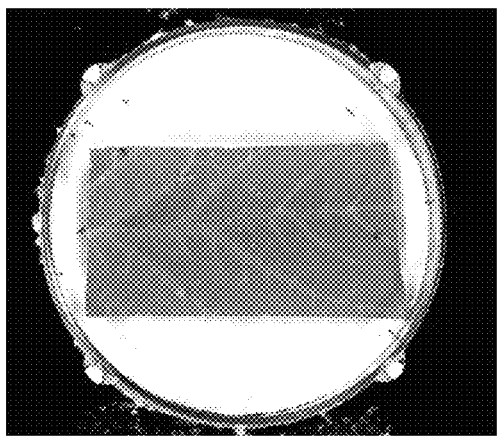
FIG. 4 shows the bioassay effect of the transgenic soybean event DBN8002 against *Spodoptera litura* in the nucleic acid sequences for detecting the soybean plant DBN8002 and detection methods thereof according to the present invention.
Figure 4:
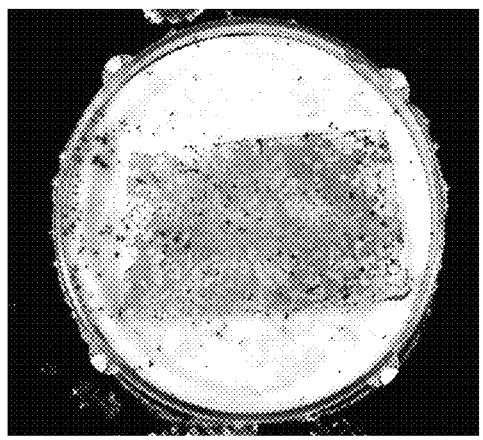
Figure 5:
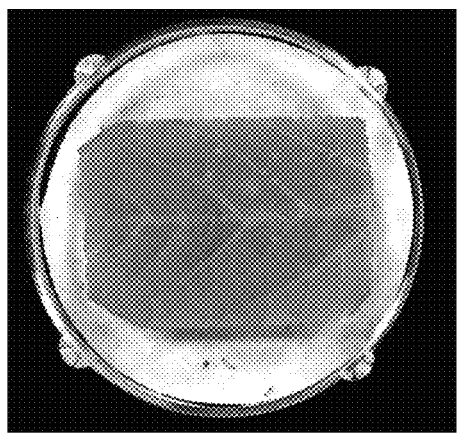
FIG. 5 shows the bioassay effect of the transgenic soybean event DBN8002 against *Spodoptera exigua* in the nucleic acid sequences for detecting the soybean plant DBN8002 and detection methods thereof according to the present invention.
Figure 5:
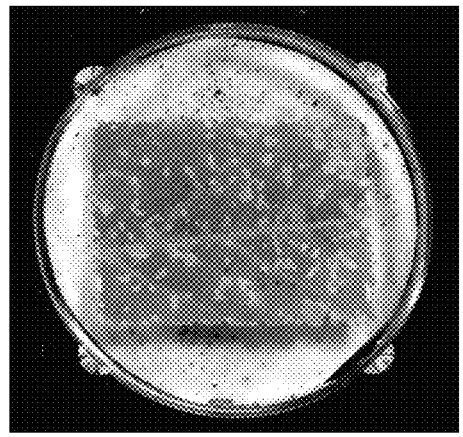
Figure 6:
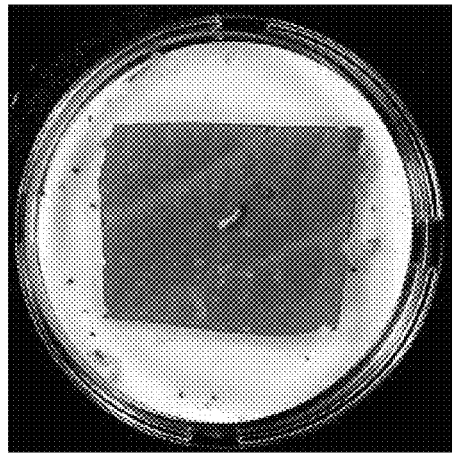
FIG. 6 shows the bioassay effect of the transgenic soybean event DBN8002 against *Clanis bilineata* in the nucleic acid sequences for detecting the soybean plant DBN8002 and detection methods thereof according to the present invention.
Figure 6:

A recombinant expression vector pDBN4006 (as shown in FIG. 2) was constructed by using standard gene cloning techniques. Vector pDBN4006 comprises two transgenic expression cassettes arranged in tandem: the first expression cassette consisting of an *Arabidopsis* ACTIN2 promoter (prAtAct2), operably linked to the insect resistant mVip3Aa gene of *Bacillus thuringiensis* (CN103509808B), further operably linked to a nopaline synthetase terminator (tNos); the second expression cassette consisting of a cauliflower mosaic virus 35S promoter (pr35S), operably linked to a glufosinate tolerant phosphinothricin-N-acetyltransferase gene (cPAT) of *Streptomyces*, further operably linked to a cauliflower mosaic virus 35S transcriptional terminator (t35S).

*Agrobacterium* LBA4404 (Invitrogen, Chicago, USA; Cat. No: 18313-015) was transformed with the vector pDBN4006 by liquid nitrogen method, and 4-[hydroxy (methyl)phosphinyl]-DL-homoalanine was used as a selective marker for screening transformed cells.

1.2 Plant Transformation

Transformation was performed by a conventional *Agrobacterium*-mediated transformation method, comprising: co-culturing the sterile-cultured soybean cotyledonary node tissues with *Agrobacterium* as described in Example 1.1 to transfer the T-DNA in the recombinant expression vector pDBN4006 into the soybean chromosomes, so as to produce the transgenic soybean event DBN8002.

Briefly, the *Agrobacterium*-mediated soybean transformation comprises: germinating mature soybean seeds in a soybean germination medium (3.1 g/L B5 salt, B5 vitamin, 20 g/L sucrose, and 8 g/L agar; pH 5.6); inoculating the seeds onto the germination medium; and culturing them under the conditions of: a temperature of $25\pm1°$ C. and a photoperiod (light/dark) of 16 h/8 h; at 4-6 days after germination, collecting fresh green soybean sterile plantlets with inflated cotyledonary node; excising the hypocotyls approximately 3-4 mm below the cotyledonary node; making longitudinal cuts through the cotyledons, and removing apical buds, lateral buds and seminal roots; wounding at the cotyledonary node with the back of a surgical blade, and contacting the wounded cotyledonary node tissues with an *Agrobacterium* suspension; wherein *Agrobacterium* can deliver the nucleotide sequence of mVip3Aa gene and the nucleotide sequence of PAT gene to the wounded cotyledonary node tissues (step 1: infection step). In this step, the cotyledonary node tissues were preferably immersed in the *Agrobacterium* suspension ($OD_{660}$=0.5-0.8, infection medium (2.15 g/L MS salt, B5 vitamin, 20 g/L sucrose, 10 g/L glucose, 40 mg/L acetosyringone (AS), 4 g/L 2-morpholine ethanesulfonic acid (MES), and 2 mg/L zeatin (ZT); pH 5.3) to start the infection. The cotyledonary node tissues were co-cultured with *Agrobacterium* for a period of time (3 days) (step 2: co-culture step). Preferably, the cotyledonary node tissues were cultured in a solid medium (containing 4.3 g/L MS salt, B5 vitamin, 20 g/L sucrose, 10 g/L glucose, 4 g/L MES, 2 mg/L ZT, and 8 g/L agar; pH 5.6) after the infection step. After the co-culture step, there may be an optional "recovery" step. In the "recovery" step, the recovery medium (3.1 g/L B5 salt, B5 vitamin, 1 g/L MES, 30 g/L sucrose, 2 mg/L ZT, 8 g/L of agar, 150 mg/L cephalosporin, 100 mg/L glutamic acid, and 100 mg/L aspartic acid; pH 5.6) comprises at least one antibiotic (150-250 mg/L cephalosporin) known to inhibit the growth of *Agrobacterium*, while does not comprise any selective agent for plant transformants (step 3: recovery step). Preferably, the tissue blocks regenerated from the cotyledonary node were cultured in a solid medium comprising antibiotic but no selective agent to eliminate *Agrobacterium* and provide a recovery stage for the infected cells. Subsequently, the tissue blocks regenerated from the cotyledonary node were cultured on a medium containing a selective agent (4-[(hydroxy (methyl)phosphinyl)]-DL-homoalanine), and the growing transformed calli were selected (step 4: selection step). Preferably, the tissue blocks regenerated from the cotyledonary node were cultured in a solid selective medium (3.1 g/L B5 salt, B5 vitamin, 1 g/L MES, 30 g/L sucrose, 1 mg/L 6-benzyladenine (6-BAP), 8 g/L agar, 150 mg/L cephalosporin, 100 mg/L glutamic acid, 100 mg/L aspartic acid, and 10 mg/L 4-(hydroxy(methyl)phosphinyl)-DL-homoalanine; pH 5.6) comprising a selective agent, which resulted in the continuous growth of the transformed cells. Then, the transformed cells regenerated into plants (step 5: regeneration step). Preferably, the tissue blocks regenerated from the cotyledonary node growing on the medium containing a selective agent were cultured in a solid medium (B5 differentiation medium and B5 rooting medium) to regenerate plants.

The resistant tissues obtained from screening were transferred to B5 differentiation medium (3.1 g/L B5 salt, B5 vitamin, 1 g/L MES, 30 g/L sucrose, 1 mg/L ZT, 8 g/L agar, 150 mg/L cephalosporin, 50 mg/L glutamic acid, 50 mg/L aspartic acid, 1 mg/L gibberellin, 1 mg/L auxin, and 5 mg/L 4-(hydroxy(methyl)phosphinyl)-DL-homoalanine; pH 5.6), and cultured for differentiation at 25° C. The differentiated plantlets were transferred to B5 rooting medium (3.1 g/L B5 salt, B5 vitamin, 1 g/L MES, 30 g/L sucrose, 8 g/L agar, 150 mg/L cephalosporin, and 1 mg/L indole-3-butyric acid (IBA)), and cultured at 25° C. When the plantlets reached about 10 cm in height, they were moved to greenhouse and cultured until fruiting. In the greenhouse, they were cultured at 26° C. for 16 hours and then at 20° C. for 8 hours per day.

1.3. Identification and Screening of Transgenic Events

A total of 288 independent transgenic $T_0$ plants were produced. In order to screen out a transgenic event with optimum performance, the above 288 independent transgenic $T_0$ single plants were moved into the greenhouse for transplantation, cultivation and propagation to afford transgenic $T_1$ single plants.

Since the genetic transformation process of soybean using mature soybean seeds and glufosinate as a selective agent tends to generate false-positive transgenic events, the $T_1$ generation was sprayed with glufosinate to identify positive transgenic events, and a total of 154 positive transgenic single plants were obtained. By TaqMan™ analysis, the above 154 transgenic soybean plants were detected for the presence of single-copy mVip3Aa and PAT genes and the absence of backbone sequences of the vector; and a total of 90 transgenic single plants were obtained. By analysis of the transgenic insertion sites, a total of 24 transgenic single plants were obtained by screening, in which the sequences on both sides of T-DNA were intact, the T-DNA was not inserted into important genes of the soybean genome and the gene insertion did not result in any large open reading frame (ORF). By evaluation and comparison of the resistance against major target insects (such as *Helicoverpa armigera* (Hubner), *Prodenia litura*, and *Spodoptera exigua*), a total of 21 transgenic single plants with good insect resistance were obtained by screening. Since genetic transformation and gene insertion may affect agronomic traits of soybean plants (such as seedling vigor, propagation period, plant height or lodging), the above 21 transgenic $T_2$-generation single plants were planted in a field to identify the agronomic trait performance of the transgenic T2 single plants at different stages (seedling stage to full flowering stage, initial grain-forming stage to maturity stage). By means of selfing and backcross breeding, it is screened whether the agronomic traits, molecular biology, resistance against the target insects and glufosinate herbicide tolerance of the transgenic soybean plants can be stably inherited under the conditions of different generations, different geographical environments and/or different background materials, and the transgenic soybean event DBN8002 was selected as an excellent event, which has a single copy of the transgenes (see Example 2), good insect resistance, glufosinate herbicide tolerance and agronomic trait performance (see Examples 6 and 7).

Example 2: Detection of the Transgenic Soybean Event DBN8002 by TaqMan

Using a plant DNA extraction kit (DNeasy Plant Maxi Kit, Qiagen), the genomic DNA was extracted from the leaf (about 100 mg) of the transgenic soybean event DBN8002 as a sample, and the copy numbers of mVip3Aa and PAT genes were detected by a fluorescent quantitative PCR method using Taqman probe. Meanwhile, a wild-type soybean plant as a control was subject to the detection and analysis according to the above methods. Experiments were carried out in triplicate and the average value was calculated.

The specific method is as follows:
  Step 1: 100 mg leaf of the transgenic soybean event DBN8002 was ground to a homogenate in a mortar with liquid nitrogen, and each sample was prepared in triplicate;
  Step 2: the genomic DNAs of the above samples were extracted using a plant DNA extraction kit (DNeasy Plant Maxi Kit, Qiagen, for detailed methods, please refer to the Product Instructions);
  Step 3: the concentrations of the genomic DNAs of the above samples were measured using ultra micro-spectrophotometer (NanoDrop 2000, Thermo Scientific);
  Step 4: the concentrations of the genomic DNAs of the above samples were adjusted to the same concentration value ranging from 80 to 100 ng/µL;
  Step 5: the copy number of the samples was identified by a fluorescent quantitative PCR method using Taqman probe, wherein the identified sample with a known copy number was used as a standard and a sample from a wild-type soybean plant was used as control. Each sample was tested in triplicate and the average value was calculated. The sequences of primers and probes for fluorescent quantitative PCR are as follows:

The following primers and probe are used for detecting the sequence of mVip3Aa gene:
  Primer 1: cgaatacagaaccctgtcggc as set forth in SEQ ID NO: 16 in SEQUENCE LISTING;
  Primer 2: cgtgaggaaggtctcagaaatgac as set forth in SEQ ID NO: 17 in SEQUENCE LISTING;
  Probe 1: cgacgatggcgtgtatatgcctcttgg as set forth in SEQ ID NO: 18 in SEQUENCE LISTING;

The following primers and probe are used for detecting the sequence of PAT gene:
  Primer 3: gagggtgttgtggctggtattg as set forth in SEQ ID NO: 19 in SEQUENCE LISTING;
  Primer 4: tctcaactgtccaatcgtaagcg as set forth in SEQ ID NO: 20 in SEQUENCE LISTING;
  Probe 2: cttacgctgggccctggaaggctag as set forth in SEQ ID NO: 21 in SEQUENCE LISTING.

| PCR reaction system comprises: | |
|---|---|
| JumpStart ™ Taq ReadyMix ™ (Sigma) | 10 µL |
| 50 × primer/probe mix | 1 µL |
| Genomic DNA | 3 µL |
| Double distilled water (ddH$_2$O) | 6 µL | wherein the 50× primer/probe mix comprises 45 µl of each primer at a concentration of 1 mM, 50 µl of the probe at a concentration of 100 µM, and 860 µl of 1×TE buffer (10 mM Tris-HCl, 1 mM EDTA; pH 8.0), and was stored in an amber tube at 4° C.

| PCR reaction condition comprises: | | |
|---|---|---|
| Step | Temperature | Time |
| 1 | 95° C. | 5 minutes |
| 2 | 95° C. | 30 seconds |
| 3 | 60° C. | 1 minute |
| 4 | go back to step 2 and repeat 40 times | |

Data was analyzed using fast real-time fluorescent quantitative PCR system software (Applied Biosystems 7900HT Fast Real-Time PCR System SDS v2.3, Applied Biosystems). The results demonstrate that the resultant transgenic soybean event DBN8002 is a single copy.

Example 3: Analysis of the Insertion Site of the Transgenic Soybean Event DBN8002

3.1 Extraction of Genomic DNA

DNA was extracted by the conventional CTAB (cetyl trimethyl ammonium bromide) method: after 2 g young leaf of the transgenic soybean event DBN8002 was ground to powder in liquid nitrogen, 0.5 mL CTAB DNA extraction buffer (20 g/L CTAB, 1.4 M NaCl, 100 mM Tris-HCl, and 20 mM EDTA (edetic acid), with a pH adjusted to pH 8.0 with NaOH) preheated at 65° C. was added, then they were mixed thoroughly and extracted at 65° C. for 90 min; 0.5 volume of phenol and 0.5 volume of chloroform were added and mixed by inversion; the mixture was centrifuged at 12,000 rpm (revolution per minute) for 10 min; the supernatant was pipetted and 2 volumes of absolute ethanol was added; the centrifuge tube was gently shaken and then left standing at 4° C. for 30 min; the centrifuge tube was centrifuged again at 12,000 rpm for 10 min such that DNA was collected to the bottom of the tube; the supernatant was discarded, and the pellet was washed with 1 mL of 70% (mass concentration) ethanol; the mixture was centrifuged at 12,000 rpm for 5 min; the pellet was dried in vacuum or blown dry on a super clean bench; and the resultant DNA pellet was dissolved in an appropriate amount of TE buffer and stored at −20° C.

3.2 Analysis of Flanking DNA Sequences

The concentration of the above extracted DNA sample was measured. The concentration of the sample to be tested is 80-100 ng/µL. The genomic DNA was digested using restriction enzymes EcoR I (5' end analysis) and EcoR V (3' end analysis) respectively. Each enzymatic digestion system was added with 26.5 µL of genomic DNA, 0.5 µL of the above restriction enzymes and 3 µL of enzymatic digestion buffer (all employed restriction enzymes are enzymes with assorted buffers thereof or generic buffers from NEB company (now known as NEBCutSmart)), and was digested for 1 hour. After digestion, the enzymatic digestion system was added with 70 µL of absolute ethanol, kept in ice bath for 30 min, and centrifuged at 12,000 rpm for 7 min. After discarding the supernatant, the pellet was blow-dried, then added with 8.5 µL of double distilled water, 1 µL of 10×T$_4$-DNA ligase buffer (NEB T4 DNA Ligase Reaction Buffer; for its specific formulation, please visit the websites of NEB or refer to https://www.neb.com/products/restriction-endonucleases or https://www.neb.com/products/b0202-t4-dna-ligase-reaction-buffer) and 0.5 µL of T4-DNA ligase, and then ligated overnight at 4° C. The 5' and 3' end genomic DNAs were isolated by PCR amplification using a series of nested primers. Specifically, the primer combination for isolating the 5' end genomic DNA comprises SEQ ID NO: 13 and SEQ ID NO: 26 as first primers, SEQ ID NO: 27 and SEQ ID NO: 28 as second primers, and SEQ ID NO: 13 as a sequencing primer. The primer combination for isolating 3' end genomic DNA comprises SEQ ID NO: 15 and SEQ ID NO: 29 as first primers, SEQ ID NO: 30 and SEQ ID NO: 31 as second primers, and SEQ ID NO: 15 as a sequencing primer. PCR reaction conditions were shown in Table 3.

The amplification product resulted from the above PCR amplification was subject to electrophoresis on an agarose gel with a mass fraction of 2.0% to isolate the PCR amplification product; subsequently, the target fragment was isolated from agarose matrix using a gel extraction kit (QIAquick Gel Extraction Kit, catalog #_28704, Qiagen Inc., Valencia, CA). Then the purified PCR amplification product was sequenced (e.g., using ABI Prism™ 377, PE Biosystems, Foster City, CA) and analyzed (e.g., using DNASTAR sequence analysis software, DNASTAR Inc., Madison, WI).

The 5' and 3' flanking sequences and junction sequences were confirmed using standard PCR procedures. The 5' flanking and junction sequences were confirmed using SEQ ID NO: 8 or SEQ ID NO: 12 in combination with SEQ ID NO: 9, SEQ ID NO: 13 or SEQ ID NO: 26. The 3' flanking and junction sequences were confirmed using SEQ ID NO: 11 or SEQ ID NO: 14 in combination with SEQ ID NO: 10, SEQ ID NO: 15 or SEQ ID NO: 29. PCR reaction systems and amplification conditions were shown in Tables 2 and 3. It will be recognized by those skilled in the art that other primer sequences could also be used to confirm the flanking and junction sequences.

DNA sequencing of the PCR amplification products provides a DNA that could be used to design other DNA molecules which could be used as primers and probes for identifying soybean plants or seeds derived from the transgenic soybean event DBN8002.

The inserted sequence of the transgenic soybean event DBN8002 was found to be flanked on the right border (5' flanking sequence) by the soybean genomic sequence shown in the nucleotides 1-647 of SEQ ID NO: 5 and flanked on the left border (3' flanking sequence) by the soybean genomic sequence shown in the nucleotides 6647-7344 of SEQ ID NO: 5. The 5' junction sequence was set forth in SEQ ID NO: 1 and the 3' junction sequence was set forth in SEQ ID NO: 2.

3.3. PCR Assay for Zygosity

Junction sequence is a relatively short polynucleotide molecule, which is a new DNA sequence and is diagnostic for the DNA of the transgenic soybean event DBN8002 when detected in polynucleotide detection and analysis. The junction sequences in SEQ ID NO: 1 and SEQ ID NO: 2 respectively are 11 polynucleotides on either side of the insertion site of the transgenic fragment and soybean genomic DNA in the transgenic soybean event DBN8002. Longer or shorter polynucleotide junction sequences can be selected from SEQ ID NO: 3 or SEQ ID NO: 4. The junction sequences (SEQ ID NO: 1 used as 5' junction region, and SEQ ID NO: 2 used as 3' junction region) were useful in the method for detecting DNA as DNA probes or DNA primer molecules. The junction sequences SEQ ID NO: 6 and SEQ ID NO: 7 were also new DNA sequences of the transgenic soybean event DBN8002, and could also be used for detecting the presence of the transgenic soybean event DBN8002 as DNA probes or DNA primer molecules. SEQ ID NO: 6 (the nucleotides 911-1129 of SEQ ID NO: 3) spans a DNA sequence and a prAtAct2 transcription origin sequence in the pDBN4006 construct, and SEQ ID NO: 7 (the nucleotides 1-243 of SEQ ID NO: 4) spans a t35S transcriptional termination sequence and a DNA sequence in the pDBN4006 construct.

Furthermore, an amplicon was generated by using at least one primer derived from SEQ ID NO: 3 or SEQ ID NO: 4, and said primer, when used in a PCR method, generated an amplicon diagnostic for the transgenic soybean event DBN8002.

Specifically, the PCR amplification product was generated from the 5' end of the transgenic inserted sequence, comprising a portion of the genomic DNA at 5' end flanking the T-DNA inserted sequence in the genome of plant materials derived from the transgenic soybean event DBN8002. The PCR amplification product comprises SEQ ID NO: 3. For PCR amplification, primer 5 (SEQ ID NO: 8), which may hybridize to a genomic DNA sequence at 5' end flanking the transgenic inserted sequence, and primer 6 (SEQ ID NO: 9), which was in pair with primer and located in the prAtAct2 transcription origin sequence of the T-DNA inserted sequence, were designed.

The PCR amplification product was generated from the 3' end of the transgenic inserted sequence, comprising a portion of the genomic DNA at 3' end flanking the T-DNA inserted sequence in the genome of plant materials derived from the transgenic soybean event DBN8002. The PCR product comprises SEQ ID NO: 4. For PCR amplification, primer 7 (SEQ ID NO: 10), which was located in the t35S transcriptional termination sequence of the T-DNA inserted sequence and primer 8 (SEQ ID NO: 11), which was in pair with primer 7 and may hybridize to a genomic DNA sequence at 3' end flanking the transgenic inserted sequence, were designed.

DNA amplification conditions described in Tables 2 and 3 could be used in the above PCR assays for zygosity to generate an amplicon diagnostic for the transgenic soybean event DBN8002. Detection of amplicons could be conducted by using a thermocycler such as Stratagene Robocycler, MJ Engine, Perkin-Elmer 9700, or Eppendorf Mastercycler Gradient, or by the methods and apparatus known to those skilled in the art.

TABLE 2

The steps and conditions of reaction mixture in the PCR reaction for the identification of the 5' end transgenic insert/genomic junction region of the transgenic soybean event DBN8002

| Step | Reagent | Amount | Note |
|---|---|---|---|
| 1 | Nuclease-free water | Added to a final volume of 20 µL | |
| 2 | 10 × reaction buffer (with MgCl$_2$) | 2.0 µL | The final concentration of 1 × buffer; the final concentration of MgCl$_2$: 1.5 mM |

TABLE 2-continued

The steps and conditions of reaction mixture in the PCR reaction for the identification of the 5' end transgenic insert/genomic junction region of the transgenic soybean event DBN8002

| Step | Reagent | Amount | Note |
|---|---|---|---|
| 3 | 10 mM solution of dATP, dCTP, dGTP and dTTP | 0.2 μL | The final concentration of each dNTP: 200 μM |
| 4 | Primer 5 (SEQ ID NO: 8) resuspended in 1 × TE buffer or nuclease-free water to a concentration of 10 μM | 0.2 μL | The final concentration: 0.1 μM |
| 5 | Primer 6 (SEQ ID NO: 9) resuspended in 1 × TE buffer or nuclease-free water to a concentration of 10 μM | 0.2 μL | The final concentration: 0.1 μM |
| 6 | RNase; DNase-free (500 μg/ml) | 0.1 μL | 50 ng/reaction |
| 7 | REDTaq ® DNA polymerase (1 unit/μL) | 1.0 μL | 1 unit/reaction (recommended to change a pipette prior to next step) |
| 8 | Extracted DNA (Template): leaves of the samples to be analyzed | | 200 ng of genomic DNA |
| | Negative control | | 50 ng of non-transgenic soybean genomic DNA |
| | Negative control | | No template DNA (the solution for resuspending DNA) |
| | Positive control | | 50 ng of soybean genomic DNA comprising DBN8002 |

TABLE 3

| Amplification conditions of thermocycler | |
|---|---|
| Cycle No. | Setting |
| 1 | 94° C. 3 min |
| 34 | 94° C. 30 sec |
| | 64° C. 30 sec |
| | 72° C. 1 min |
| 1 | 72° C. 10 min |

The reaction solutions were gently mixed, and if there is no hot top on thermocycler, added with 1-2 drops of mineral oil on the top of each reaction solution. PCR reaction was conducted in a thermocycler such as Stratagene Robocycler (Stratagene, La Jolla, CA), MJ Engine (MJ R-Biorad, Hercules, CA), Perkin-Elmer 9700 (Perkin Elmer, Boston, MA), or Eppendorf Mastercycler Gradient (Eppendorf, Hamburg, Germany) using the cycle parameters shown in Table 3. MJ Engine or Eppendorf Mastercycler Gradient thermocycler should be run in the calculated mode. The Perkin-Elmer 9700 thermocycler should have a ramp speed set at maximum when running.

The experiments show the following results: when used in a PCR reaction of the transgenic soybean event DBN8002 genomic DNA, primers 5 and 6 (SEQ ID NO: 8 and 9) result in a 1524 bp fragment of amplification product, but when the primers were used in PCR reactions of a non-transformed soybean genomic DNA and non-DBN8002 soybean genomic DNA, no fragment was amplified; when used in a PCR reaction of the transgenic soybean event DBN8002 genomic DNA, primers 7 and 8 (SEQ ID NO: 10 and 11) result in a 656 bp fragment of amplification product, but when the primers were used in PCR reactions of a non-transformed soybean genomic DNA and non-DBN8002 soybean genomic DNA, no fragment was amplified.

PCR assays for zygosity could also be used to identify whether the material derived from the transgenic soybean event DBN8002 is homozygous or heterozygous. Primer 9 (SEQ ID NO: 12), primer 10 (SEQ ID NO: 13) and primer 11 (SEQ ID NO: 14) were used in an amplification reaction to produce an amplicon diagnostic for the transgenic soybean event DBN8002. DNA amplification conditions described in Tables 4 and 5 could be used in the above assays for zygosity to produce an amplicon diagnostic for the transgenic soybean event DBN8002.

TABLE 4

| Reaction solution for the assays for zygosity | | | |
|---|---|---|---|
| Step | Reagent | Amount | Note |
| 1 | Nuclease-free water | Added to a final volume of 5 μL | |
| 2 | 2 × Universal Master Mix (Applied Biosystems Catalog No. 4304437) | 2.5 μL | 1 × final concentration |
| 3 | Primer 9 (SEQ ID NO: 12) and primer 10 (SEQ ID NO: 13) resuspended in nuclease-free water to a concentration of 10 μM | 0.05 μL | The final concentration: 0.25 μM |
| 4 | Primer 11 (SEQ ID NO: 14) resuspended in 1 × TE buffer or nuclease-free water to a concentration of 10 μM | 0.01 μL | The final concentration: 0.15 μM |
| 5 | REDTaq ® DNA polymerase (1 unit/μl) | 1.0 μl (recommended to change a pipette prior to next step) | 1 unit/reaction |
| 6 | Extracted DNA (template): leaves of the samples to be analyzed | 200 ng of genomic DNA | |
| | Negative control | 50 ng of non-transgenic soybean genomic DNA | |

TABLE 4-continued

Reaction solution for the assays for zygosity

| Step | Reagent | Amount | Note |
|------|---------|--------|------|
| | Negative control | No template DNA (the solution for resuspending DNA) | |
| | Positive control | 50 ng of soybean genomic DNA comprising DBN8002 | |

TABLE 5

Thermocycler amplification conditions for the assays for zygosity

| Cycle No. | Setting |
|-----------|---------|
| 1 | 95° C. 10 min |
| 10 | 95° C. 15 sec |
| | 64° C. 1 min (−1° C./cycle) |
| 30 | 95° C. 15 sec |
| | 54° C. 1 min |
| 1 | 10° C. immersion |

PCR reaction was conducted in a thermocycler such as Stratagene Robocycler (Stratagene, La Jolla, CA), MJ Engine (MJ R-Biorad, Hercules, CA), Perkin-Elmer 9700 (Perkin Elmer, Boston, MA), or Eppendorf Mastercycler Gradient (Eppendorf, Hamburg, Germany) using the cycle parameters shown in Table 5. MJ Engine or Eppendorf Mastercycler Gradient thermocycler should be run in the calculated mode. The Perkin-Elmer 9700 thermocycler should have a ramp speed set at maximum when running.

In the amplification reaction, the biological sample comprising template DNA contains the DNA diagnostic for the presence of the transgenic soybean event DBN8002. Alternatively, the amplification reaction would result in two different DNA amplicons generated from the biological sample comprising the DNA derived from soybean genome, and the DNA derived from soybean genome is heterozygous for the corresponding allele of the inserted DNA present in the transgenic soybean event DBN8002. The two different amplicons would correspond to a first amplicon (SEQ ID NO: 12 and SEQ ID NO: 14) derived from the locus of wild-type soybean genome and a second amplicon (SEQ ID NO: 12 and SEQ ID NO: 13) diagnostic for the presence of the transgenic soybean event DBN8002 DNA. A soybean DNA sample that only generates a single amplicon corresponding to the second amplicon as described in regard to heterozygous genome could be diagnosed as the presence of the transgenic soybean event DBN8002 in that sample, and the sample was produced from soybean seeds homozygous for the corresponding allele of the insert DNA present in the transgenic soybean plant DBN8002.

It should be noted that the primer pairs for the transgenic soybean event DBN8002 are used to produce an amplicon diagnostic for genomic DNA of the transgenic soybean event DBN8002.

These primer pairs include but are not limited to primers 5 and 6 (SEQ ID NO: 8 and SEQ ID NO: 9), and primers 7 and 8 (SEQ ID NO: 10 and SEQ ID NO: 11), and are used in the DNA amplification method. In addition, control primers 12 and 13 (SEQ ID NOs: 22 and 23) for amplification of an endogenous soybean gene are included as an internal standard for reaction conditions. The analysis of the DNA extraction sample of the transgenic soybean event DBN8002 should include a tissue DNA extract from the transgenic soybean event DBN8002 as positive control, a DNA extract from a soybean plant that is not the transgenic soybean event DBN8002 as negative control, and a negative control without template soybean DNA extract. In addition to these primer pairs, any primer pair from SEQ ID NO: 3 or a complementary sequence thereof, or SEQ ID NO: 4 or a complementary sequence thereof, can be used. When these primers are used for DNA amplification reaction, they respectively produce amplicons comprising SEQ ID NO: 1 or SEQ ID NO: 2 and are diagnostic for tissues derived from the transgenic soybean event DBN8002. DNA amplification conditions as described in Tables 2 to 5 can be used in the production of an amplicon diagnostic for the transgenic soybean event DBN8002 by using suitable primer pairs. The DNA extract of soybean plants or seeds which produces an amplicon diagnostic for the transgenic soybean event DBN8002 in a DNA amplification method and is presumed to contain the transgenic soybean event DBN8002, or a product derived from the transgenic soybean event DBN8002 can be used as a template for amplification to determine the presence of the transgenic soybean event DBN8002.

Example 4: Detection of the Transgenic Soybean Event DBN8002 by Southern Blot 4.1 DNA Extraction for Use in Southern Blot Approximately 5 to 10 g of plant tissue was ground in liquid nitrogen using a mortar and a pestle. 4 to 5 g of the ground plant tissue was resuspended in 20 mL of CTAB lysis buffer (100 mM Tris-HCl pH 8.0, 20 mM EDTA pH 8.0, 1.4 M NaCl, 0.2% v/v β-mercaptoethanol, 2% w/v CTAB), and incubated at a temperature of 65° C. for 60 minutes. During incubation, the sample was uniformly mixed by inversion once per 10 minutes. After incubation, an equal volume of phenol/chloroform/isoamyl alcohol (25:24:1) was added, and gently mixed by inversion for extraction, and then centrifuged at a rotation speed of 4,000 rpm for 20 minutes. The aqueous phase was collected and re-extracted once with an equal volume of chloroform/isoamyl alcohol (24:1). The aqueous phase was re-collected and added with an equal volume of isopropanol. The mixture was mixed uniformly, left standing at a temperature of −20° C. for 1 hour to precipitate DNA, and then centrifuged at a rotation speed of 4,000 rpm for 5 minutes to obtain the DNA pellet, which was subsequently resuspended in 1 mL of TE buffer (10 mM Tris-HCl, 1 mM EDTA; pH 8.0). In order to degrade any possible RNA, the DNA was incubated with 40 μL of 10 mg/mL RNase A at a temperature of 37° C. for 30 minutes, centrifuged at a rotation speed of 4,000 rpm for 5 minutes, and then centrifuged at a rotation speed of 12,000 rpm for 10 minutes in the presence of 0.1-fold volume of 3 M sodium acetate (pH 5.2) and 2-fold volumes of absolute ethanol to precipitate DNA. After the supernatant was discarded, the pellet was washed with 1 mL of 70% (v/v) ethanol and dried under room temperature, and then the DNA was re-dissolved in 1 mL of TE buffer.

4.2 Restriction Enzyme Digestion

The concentration of genomic DNA in the above-mentioned sample was measured by using an ultra micro-volume spectrophotometer (NanoDrop 2000, Thermo Scientific).

In a 100 μL of reaction system, 5 μg DNA was digested each time. Genomic DNA was digested respectively with restriction enzymes Mfe I and Nco I, using a portion of the sequences of mVip3Aa and PAT genes in T-DNA as probes. For each enzyme, the digestion products were incubated overnight at an appropriate temperature. The sample was spun in a centrifugal vacuum concentrator (speed Vacuum, Thermo Scientific) to reduce the volume to 20 μl.

4.3 Gel Electrophoresis

Bromophenol blue loading dye was added to each sample from Example 4.2, and each sample was loaded onto a 0.7% agarose gel containing ethidium bromide and electrophoresed for isolation in TAE electrophoresis buffer (40 mM Tris-acetic acid, 2 mM EDTA, pH 8.5). The gel electrophoresis was run overnight at a voltage of 20 V.

After the electrophoresis, the gel was treated with 0.25 M HCl for 10 minutes to depurinate the DNA, and then treated with a denaturation solution (1.5 M NaCl, 0.5 M NaOH) and a neutralization solution (1.5 M NaCl, 0.5 M Tris-HCl; pH 7.2) for 30 minutes, respectively. 5×SSC (3 M NaCl, 0.3 M Sodium citrate; pH 7.0) was poured into a porcelain dish; a piece of glass was covered; and then a wet filter paper bridge, a gel, a positively charged nylon membrane (Roche, Cat. No. 11417240001), three pieces of filter paper, a paper tower, and a heavy object were placed successively. After membrane-transfer at room temperature overnight, the nylon membrane was rinsed with deionized water twice, and the DNA was immobilized onto the membrane by ultraviolet crosslinker (UVP, UV Crosslinker CL-1000).

4.4 Hybridization

A suitable DNA sequence was amplified by PCR for probe preparation. The DNA probes were SEQ ID NO: 24 or SEQ ID NO: 25, or partially homologous or complementary to the above sequences. The DIG labeling of the probes, Southern blot, membrane washing, and other operations were performed by using the DNA Labeling and Detection Starter Kit II (Roche, Cat. No. 11585614910). For specific methods, please refer to their Product Instructions. Finally, an X-ray film (Roche, Cat. No. 11666916001) was used to detect the position where the probe was bound.

Each Southern blot included two control samples: (1) DNA from a negative (untransformed) segregant, which was used to identify any endogenous soybean sequences that could hybridize to the element-specific probe; and (2) DNA from a negative segregant, into which Hind III-digested pDBN4006 plasmid was introduced in an amount equivalent to a single copy number based on the length of the probe, which was used as a positive control to show the sensitivity of the experiment when a single copy of gene was detected in the soybean genome.

The hybridization data provides corroboratory evidence to support TaqMan™ PCR analysis, namely, the soybean plant DBN8002 contains mVip3Aa and PAT genes in a single copy. By using the probe for mVip3Aa gene, the enzymatic digestions of Mfe I and Nco I respectively generate single bands of about 5.5 kb and 11 kb; and by using the probe for PAT gene, the enzymatic digestions of Mfe I and Nco I respectively generate single bands of about 2.5 kb and 10 kb. This indicates that mVip3Aa and PAT genes were respectively present in the soybean plant DBN8002 in one copy. Furthermore, no hybridization band was obtained using the backbone probe. This indicates that no backbone sequence of the vector pDBN4006 was introduced into the genome of the soybean plant DBN8002 during transformation.

Example 5: Detection of Protein Expression in the Transgenic Soybean Event DBN8002 by ELISA The expression ranges of Vip3Aa and PAT proteins in the transgenic soybean event DBN8002 can be detected by ELISA.

2 mg lyophilized leaf of the transgenic soybean event DBN8002 was weighed and taken as the sample. The leaf was ground in liquid nitrogen and then added with 1 mL extraction buffer (8 g/L NaCl, 0.27 g/L $KH_2PO_4$, 1.42 g/L $Na_2HPO_4$, 0.2 g/L KCl, and 5.5 ml/L Tween-20; pH 7.4). The mixture was mixed uniformly, left standing at a temperature of 4° C. for 30 minutes, and then centrifuged at a rotation speed of 12,000 rpm for 10 minutes. The supernatant was pipetted and diluted with the above extraction buffer to suitable dilution. 80 μL diluted supernatant was collected for detection by ELISA.

The protein (Vip3Aa and PAT proteins) amounts in the sample by the dry weight of leaf were measured and analyzed by ELISA (Enzyme-Linked Immunosorbent Assay) detection kits (ENVIRLOGIX Company, Vip3Aa kit (AP085) and PAT kit (AP014)). For specific methods, please refer to their Product Instructions. Meanwhile, a wild-type soybean plant leaf (non-transgenic, NGM) was used as a control sample. Detection and analysis were carried out according to the above-mentioned method, with 6 replicates per plant.

The experimental results of the protein (Vip3Aa and PAT proteins) contents of the transgenic soybean event DBN8002 were as shown in Table 6. The average expression levels of Vip3Aa proteins in the transgenic soybean event DBN8002 and wild-type soybean plant leaves by dry weight of leaf (μg/g) were 14.49 and 0, respectively; and the average expression levels of PAT proteins in the transgenic soybean event DBN8002 and wild-type soybean plant leaves by dry weight of leaf (μg/g) were 227.29 and 0, respectively.

TABLE 6

Average results of the assays on the protein expression levels (μg/g) in the transgenic soybean event DBN8002

| Protein/plant | DBN8002 | NGM |
|---|---|---|
| Vip3Aa protein | 14.49 ± 2.62 | 0 ± 0 |
| PAT protein | 227.29 ± 11.30 | 0 ± 0 |

Example 6: Detection of the Resistance of the Event Against Insects 6.1 Bioassay of the Soybean Plant DBN8002 in China Two kinds of plants, the transgenic soybean event DBN8002 and wild-type soybean plant (non-transgenic, NGM), were tested using *Helicoverpa armigera* (CBW), *Spodoptera litura* (TCW), *Spodoptera exigua* (BAW) and *Clanis bilineata* (BHM) via the following bioassays:

Top second leaves at V3 stage from two kinds of plants, the transgenic soybean event DBN8002 and wild-type soybean plant (non-transgenic, NGM), were prepared respectively. They were rinsed with sterile water and aspirated to dryness with a gauze. Then with the removal of veins, soybean leaves were cut into shapes of about 2.5 cm×3 cm. 1 to 3 pieces of the leaf (the number of the leaf was determined based on the leaf intake of insect) were placed on filter paper moistened with distilled water at the bottom of round plastic Petri dishes. 10 newly hatched larvae by artificial feeding were placed in each dish. Then the Petri dishes were covered with lids and kept for 3 days under the conditions including a temperature of 26-28° C., relative humidity of 70%-80%, and a photoperiod (light/dark) of 16:8 prior to obtaining a statistic result. Three indicators, larvae development rate, mortality of tested insects and leaf damage ratio, were statistically analyzed to obtain a total score of resistant trait (full score: 300 points). The total score of resistant trait=100×mortality+[100×mortality+90×(number of newly hatched insect/a total of the inoculated larvae)+60×(number of newly hatched insects for negative control/a total of the inoculated larvae)+10×(number of insects for negative control/a total of the inoculated larvae)]+100×(1−leaf damage ratio), wherein a total of the inoculated larvae refers to the total number of the larvae inoculated, i.e. 10 larvae in each dish; the larvae development rate was reflected by the formula of the total score of resistant trait; and the leaf damage ratio refers to the proportion of insect-feeding area in total area of the leaf. For each insect, five plants from the transgenic soybean event DBN8002 and the wild-type soybean plant (non-transgenic, NGM) were tested, 6 replicates per plant. The results were shown in Tables 7-8 and FIGS. 3-6, respectively.

TABLE 7

The bioassay result of insect resistance of the transgenic soybean event DBN8002 in China-Mortality (%)

| Insect/plant | DBN8002 | NGM |
|---|---|---|
| CBW | 60 ± 12 | 7 ± 3 |
| TCW | 99 ± 1 | 3 ± 4 |
| BAW | 98 ± 1 | 4 ± 3 |
| BHM | 85 ± 6 | 7 ± 3 |

TABLE 8

The bioassay result of the insect resistance of the transgenic soybean event DBN8002-Total score of resistant trait (points).

| Insects/plants | DBN8002 | NGM |
|---|---|---|
| CBW | 198 ± 22 | 35 ± 12 |
| TCW | 289 ± 3 | 42 ± 20 |
| BAW | 286 ± 10 | 55 ± 17 |
| BHM | 284 ± 7 | 34 ± 15 |

The results show that the transgenic soybean event DBN8002 exhibits significantly higher mortality of tested insects and total score of resistant trait than the NGM, indicating that the transgenic soybean event DBN8002 has good resistance against *Helicoverpa armigera*, *Spodoptera litura*, *Spodoptera exigua* and *Clanis bilineata*.

6.2 Field Test of the Transgenic Soybean Event DBN8002 in China

The transgenic soybean event DBN8002 and wild-type soybean plant (non-transgenic, NGM) were planted in a field. Randomized block design with 3 replicates was employed. The district had an area of 30 m² (5 m×6 m), row spacing of 60 cm and plant spacing of 10 cm. The plants were conventionally cultivated and managed, avoiding spray of insecticides during the whole propagation period.

(1) *Helicoverpa armigera*

The soybeans were only subject to natural infestation in the area with serious natural occurrence of *Helicoverpa armigera* (the conditions for occurrence of natural insect damage: the most severe damage occurs from June to July and the optimum temperature for pest growth ranges from 20 to 30° C.). When the soybean plants grew to V3 stage (trifoliate), they were tracked for investigating the NGM leaves fed by larvae of *Helicoverpa armigera*. When the top second and third leaves of the NGM were not consumed, the damage area rate (the damage area rate=the sum of the leaf damage area in each single plant/the total area of plant leaves×100%) of *Helicoverpa armigera* on soybean plants was investigated one by one. The result of resistance of the transgenic soybean event DBN8002 against *Helicoverpa armigera* is shown in Table 9.

TABLE 9

The result of resistance of the transgenic soybean event DBN8002 against *Helicoverpa armigera* under the conditions of natural infestation

| Program/plant | DBN8002 | NGM |
|---|---|---|
| Damage area rate (%) | 5 ± 3 | 24 ± 7 |

Figure 7:
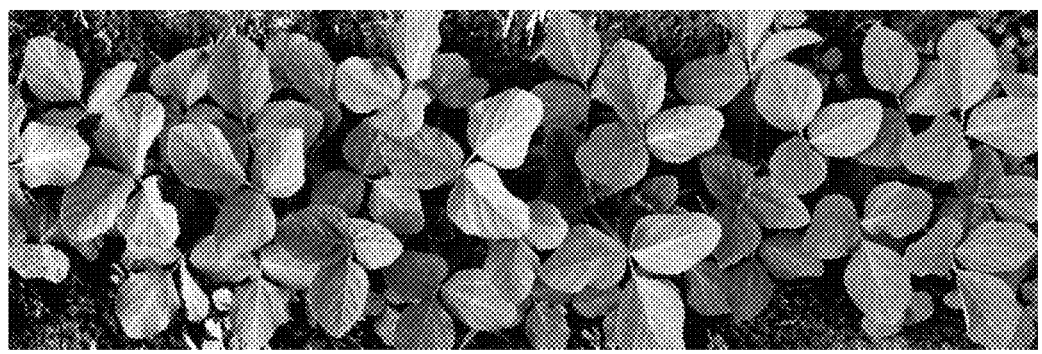
FIG. 7 shows the field effect of the transgenic soybean event DBN8002 inoculated with *Helicoverpa armigera* (Hubner) in the nucleic acid sequences for detecting the soybean plant DBN8002 and detection methods thereof according to the present invention.
Figure 7:
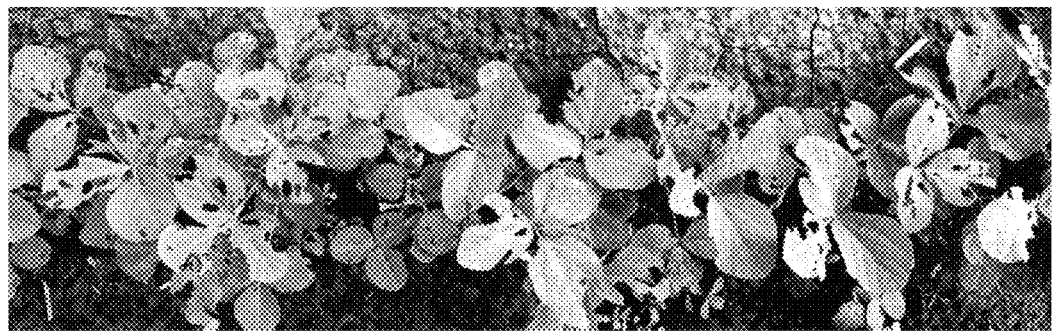

The results show that under the conditions of natural occurrence of *Helicoverpa armigera*, as compared with the NGM, the transgenic soybean event DBN8002 exhibits significantly reduced damage area rate of *Helicoverpa armigera*, thus indicating that the transgenic soybean event DBN8002 has good resistance against *Helicoverpa armigera*. The field effect of the transgenic soybean event DBN8002 under the conditions of natural occurrence of *Helicoverpa armigera* is shown in FIG. 7.

(2) *Spodoptera exigua*

The soybeans were only subject to natural infestation in the area with serious natural occurrence of *Spodoptera exigua* (the conditions for occurrence of natural insect damage: the most severe damage occurs from June to July and the optimum temperature for pest growth ranges from 20 to 30° C.). When the soybean plants grew to V3 stage, they were tracked for investigating the NGM leaves fed by larvae of *Spodoptera exigua*. When the top second and third leaves of the NGM were not consumed, the damage area rate (the damage area rate=the sum of the leaf damage area in each single plant/the total area of plant leaf×100%) of *Spodoptera exigua* on soybean plants was investigated one by one. The result of resistance of the transgenic soybean event DBN8002 against *Spodoptera exigua* is shown in Table 10.

TABLE 10

The result of resistance of the transgenic soybean event DBN8002 against *Spodoptera exigua* under the conditions of natural infestation

| Program/plant | DBN8002 | NGM |
|---|---|---|
| Damage area rate (%) | 2 ± 1 | 22 ± 4 |

Figure 8:
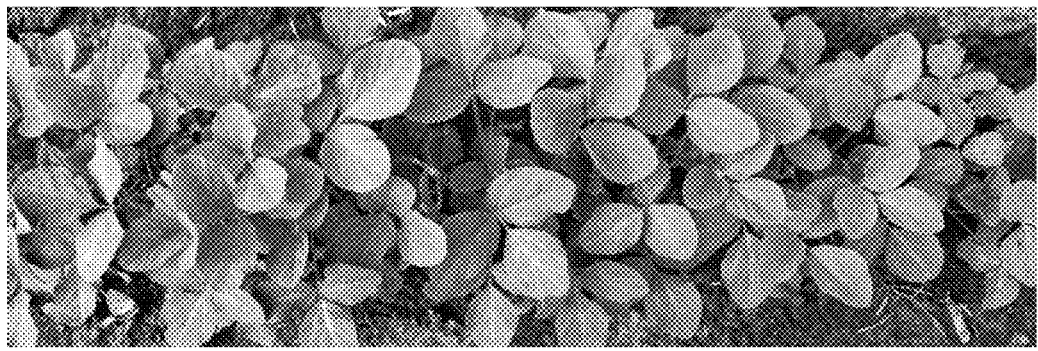
FIG. 8 shows the field effect of the transgenic soybean event DBN8002 in the nucleic acid sequences for detecting the soybean plant DBN8002 and detection methods thereof according to the present invention, under the conditions of naturally occurring *Spodoptera exigua;*
Figure 8:
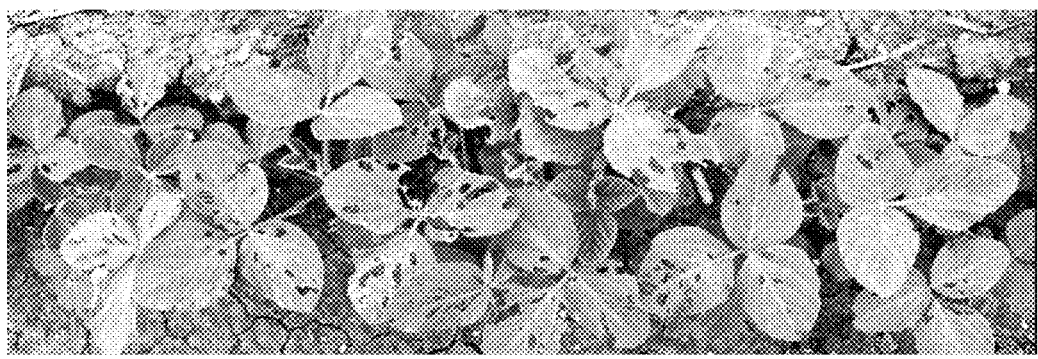

The results show that under the conditions of natural occurrence of *Spodoptera exigua*, as compared with the NGM, the transgenic soybean event DBN8002 exhibits significantly reduced damage area rate of *Spodoptera exigua*, thus indicating that the transgenic soybean event DBN8002 has good resistance against *Spodoptera exigua*. The field effect of the transgenic soybean event DBN8002 under the conditions of natural occurrence of *Spodoptera exigua* is shown in FIG. 8.

(3) *Spodoptera litura*

The artificial inoculation was carried out twice at V3 stage of soybean plants. 100 plants in the vicinity of the central region in each district were selected and subject to artificial inoculation. The top second leaf of each soybean plant was inoculated with about 10 newly hatched larvae by artificial feeding. 3 days after the inoculation, a second inoculation was carried out with the same density of larvae as the first inoculation. 5-21 days after the inoculation, the leaf areas fed by larvae of the plant were investigated one by one. The investigation was generally carried out 14 days after the inoculation. If the damage area rate (the damage area rate=the sum of the leaf damage area in each single plant/the total area of plant leaf×100%) of leaves in the NGM reached 15%, it was considered valid. If the damage area rate did not reach 15%, the investigation could be delayed properly; however, if the damage area rate still did not reach 15% after 21 days, this inoculation was considered invalid. The average value of the damage area rate of *Spodoptera litura* on soybean leaves during V3 stage of soybean plants in each district was calculated. The result of resistance of the transgenic soybean event DBN8002 against *Spodoptera litura* is shown in Table 11.

TABLE 11

The result of resistance of the transgenic soybean event DBN8002 against *Spodoptera litura* under the condition of artificial inoculation

| Program/plant | DBN8002 | NGM |
|---|---|---|
| Damage area rate (%) | 3 ± 2 | 26 ± 5 |

Figure 9:
FIG. 9 shows the field effect of the transgenic soybean event DBN8002 in the nucleic acid sequences for detecting the soybean plant DBN8002 and detection methods thereof according to the present invention, under the conditions of naturally occurring *Spodoptera litura;*
Figure 9:
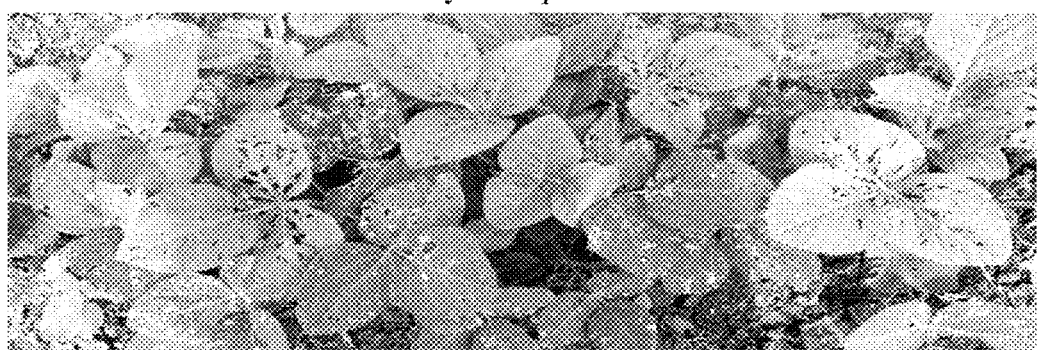

The results show that under the condition of artificial inoculation, the transgenic soybean event DBN8002 exhibits significantly lower damage area rate than NGM, thus indicating that the transgenic soybean event DBN8002 has good resistance against *Spodoptera litura*. The field effect of the transgenic soybean event DBN8002 inoculated with *Spodoptera litura* is shown in FIG. 9.

6.3 Bioassay of the Soybean Plant DBN8002 in Argentina

Figure 10:
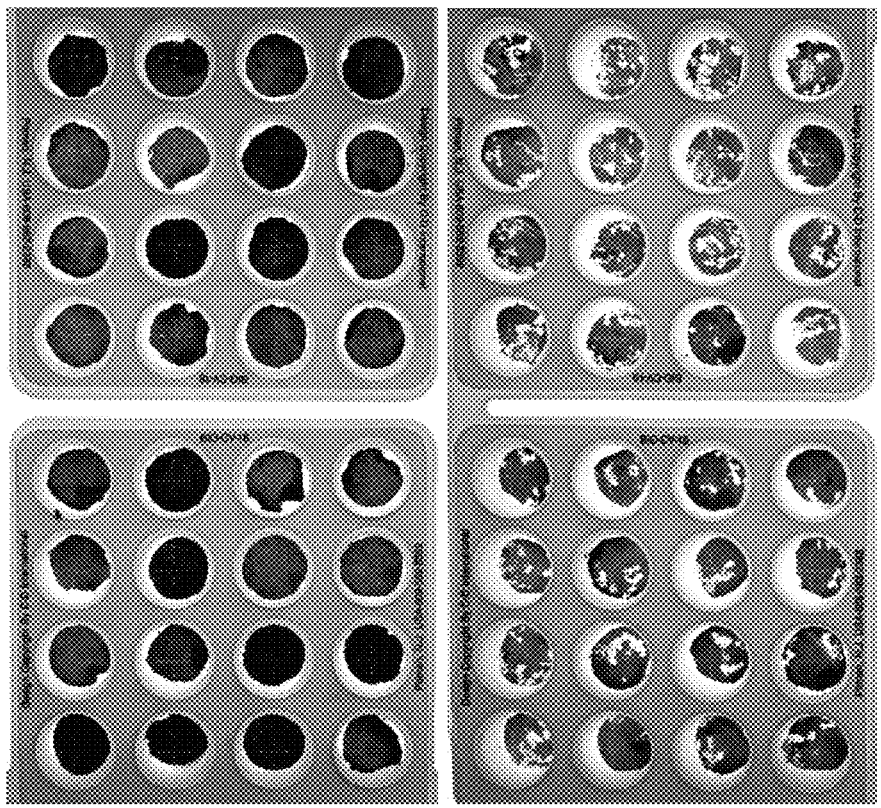
FIG. 10 shows the bioassay effect of the transgenic soybean event DBN8002 against *Spodoptera frugiperda* in the nucleic acid sequences for detecting the soybean plant DBN8002 and detection methods thereof according to the present invention.

Two kinds of plants, the transgenic soybean event DBN8002 and wild-type soybean plant (non-transgenic, NGM), were tested using Chrysodeixis includens (SBL), Rachiplusia nu, (SFL), Spodoptera frugiperda (FAW) and Spodoptera cosmioides (BLAW) via the following bioassays:

Top second leaves at V3 stage from two kinds of plants, the transgenic soybean event DBN8002 and wild-type soybean plant (non-transgenic, NGM), were prepared respectively. They were rinsed with sterile water and aspirated to dryness with a gauze. Then with the removal of veins, the soybean leaves were cut into circular shapes with a diameter of about 1 cm. 1 to 3 pieces (the number of the leaf was determined based on the leaf intake of insect) of the circular leaf were placed on filter paper moistened with distilled water in the wells of bioassay plates (as shown in FIG. 10). One newly hatched larva was placed in each well. Then the plates were covered with lids and kept for 5 days under the conditions including a temperature of 26-28° C., relative humidity of 70%-80%, and a photoperiod (light/dark) of 16:8 prior to obtaining a statistic result. Mortality of tested insects and leaf damage ratio (the leaf damage ratio refers to the proportion of leaf area fed by insects in the total area of leaf) were statistically analyzed. For each insect, 6 plants with equivalent growth vigor from the transgenic soybean event DBN8002 and wild-type soybean plant (non-transgenic, NGM) were tested, with 32 bioassay wells per plant. The results are shown in Table 12 and FIG. 10 (*Spodoptera frugiperda*).

TABLE 12

The bioassay results of the transgenic soybean event DBN8002 in Argentina

| Insect | Plant | Mortality (%) | Leaf damage ratio (%) |
|---|---|---|---|
| SBL | DBN8002 | 84.8 ± 4.3 | 0.3 ± 0.0 |
|  | NGM | 10.6 ± 3.2 | 2.7 ± 0.8 |
| SFL | DBN8002 | 77.6 ± 7.6 | 0.9 ± 0.2 |
|  | NGM | 8.9 ± 3.1 | 8.0 ± 1.2 |
| FAW | DBN8002 | 97.4 ± 2.7 | 0.1 ± 0.0 |
|  | NGM | 2.1 ± 0.5 | 10.3 ± 3.2 |
| BLAW | DBN8002 | 86.5 ± 4.3 | 0.3 ± 0.0 |
|  | NGM | 10.1 ± 5.2 | 9.6 ± 2.8 |

The results show that the transgenic soybean event DBN8002 exhibits significantly higher mortality of tested insects of the above-mentioned insect species than the NGM, indicating that the transgenic soybean event DBN8002 has good resistance against Chrysodeixis includens (SBL), Rachiplusia nu (SFL), Spodoptera frugiperda (FAW) and Spodoptera cosmioides (BLAW) (typical pests found on soybeans in South America).

6.4 Field Test of the Transgenic Soybean Event DBN8002 in Argentina

Two kinds of plants, the transgenic soybean event DBN8002 and wild-type soybean plant (non-transgenic, NGM), were planted in a field; and in vivo bioassays in field were carried out using Chrysodeixis includens (SBL), Rachiplusia nu (SFL), Anticarsia gemmatalis (VBC) and Spodoptera frugiperda (FAW) according to the following method.

Large bioassay cages (screen mesh type) were prepared in a field. Each bioassay cage was used for testing one insect only. The individual bioassay cages were not arranged in communication and they were further physically separated by artificially planted corn and weeds naturally growing in the field. The transgenic soybean event DBN8002 and wild-type soybean plant (non-transgenic, NGM) were randomly planted in each individual bioassay cage, with 3 replicates per plant type and each replicate planted in one row (row length: 3 m, 30 plants per row, row spacing: 50 cm). The plants were conventionally cultivated and managed, avoiding spray of insecticides during the whole propagation period. When the plants grew to around V5 stage (penta-foliate), suitable amount of adult insects of the above-mentioned species were released into the cage. After 10 days, the leaf damage ratio (which refers to the proportion of leaf area fed by insects in the total area of leaf) was investigated. The results are shown in Table 13.

TABLE 13

The results of resistance of the transgenic soybean event DBN8002 against pests under the condition of artificial inoculation in Argentina

| Insect | Plant | Leaf damage ratio (%) |
|---|---|---|
| SBL | DBN8002 | 2.0 ± 0.2 |
|  | NGM | 10.2 ± 2.1 |
| SFL | DBN8002 | 5.3 ± 2.5 |
|  | NGM | 35.4 ± 7.9 |
| VBC | DBN8002 | 0.3 ± 0.0 |
|  | NGM | 11.7 ± 2.3 |

TABLE 13-continued

The results of resistance of the transgenic
soybean event DBN8002 against pests under
the condition of artificial inoculation in Argentina

| Insect | Plant | Leaf damage ratio (%) |
|---|---|---|
| FAW | DBN8002 | 0.1 ± 0.0 |
|  | NGM | 9.5 ± 3.1 |

The results show that under the condition of artificial inoculation, the transgenic soybean event DBN8002 exhibits lower leaf damage rate than NGM, indicating that the transgenic soybean event DBN8002 has good resistance against Chrysodeixis includens (SBL), Rachiplusia nu (SFL), Anticarsia gemmatalis (VBC) and Spodoptera frugiperda (FAW) (typical pests found on soybeans in South America).

Example 7: Detection of Herbicide Tolerance of the Event

Basta herbicide (in which the active ingredient is 18% glufosinate aqueous solution) was selected for spray application in the experiment. Randomized block design with three replicates was employed. The district had an area of 15 m$^2$ (5 m×3 m), row spacing of 60 cm and plant spacing of 25 cm. The plants were conventionally cultivated and managed, and one-meter interval was set among the districts. The transgenic soybean event DBN8002 was subject to the following two treatments: (1) no spray application, but spraying an equal volume of clean water when spraying the herbicide during treatment (2); and (2) spray application of Basta herbicide at V2-V3 leaf stage (bi- or tri-foliate) at a dose of 800 g a.i./ha (a.i./ha means "active ingredient per hectare"). It should be noted that glufosinate herbicide (such as Basta) is a contact-type herbicide; if the herbicide is manipulated inappropriately in the field, e.g., accumulating too much herbicide solution locally, phytotoxicity symptom may occur; this does not mean that the transgenic soybean event DBN8002 has impaired tolerance; and glufosinate herbicides of various concentrations and formulations are also applicable to the following conclusion if they are converted to the above equivalent amount of the active ingredient glufosinate.

The investigation of phytotoxicity symptoms was respectively carried out at 1 week and 2 weeks after application, and the yields of the districts were determined at the time of harvest. The phytotoxicity symptom grading is shown in Table 14. The herbicide tolerance of the transformation event was assessed by using the damage rate of herbicide as an indicator. In particular, the damage rate of herbicide (%)=Σ(number of plants of the same damage level×level number)/(total number of plants×highest level), wherein the damage rate of herbicide refers to the damage rate of glufosinate, which was determined according to the result of phytotoxicity investigation two weeks after glufosinate treatment; and the tolerance level of soybean to the herbicide was assessed based on the damage rate of herbicide (glufosinate). The soybean yield of each district was obtained by weighing the total yield (by weight) of soybean grains of 3 rows in the middle of each district. The yield difference among different treatments was measured as percentage of yield. The percentage of yield (%)=yield with spray application/yield without spray application. Results of herbicide tolerance of the transgenic soybean event DBN8002 and the soybean yield are shown in Table 15.

TABLE 14

Grading standard of phytotoxicity
degree of glufosinate herbicide on soybean

| Phytotoxicity level | Description of symptoms |
|---|---|
| 1 | Regularly growing without any damage symptom |
| 2 | Slight phytotoxicity of less than 10% |
| 3 | Moderate phytotoxicity, which can be recovered later without affecting yield |
| 4 | Serious phytotoxicity, which is difficult to recover and results in reduced yield |
| 5 | Serious phytotoxicity, which cannot be recovered and results in significantly reduced yield or no yield |

TABLE 15

Results of glufosinate herbicide tolerance of the
transgenic soybean event DBN8002
and the soybean yield

| Program/plant | DBN8002 |
|---|---|
| Damage rate by glufosinate % (control) | 0 ± 0 |
| Damage rate by glufosinate % (800 g a.i./ha) | 0 ± 0 |
| percentage of yield % (800 g a.i./ha) | 99.1 ± 0.3 |

The results show that, in terms of the damage rate by glufosinate herbicide: the damage rate of the transgenic soybean event DBN8002 treated with glufosinate herbicide (800 g a.i./ha) is 0. Thus, the transgenic soybean event DBN8002 has good glufosinate herbicide tolerance.

In regards to the yield, there is no significant difference in the yields of the transgenic soybean event DBN8002 between the treatment without spray application and the treatment with spray application of 800 g a.i./ha of glufosinate. Thus, this further shows that the transgenic soybean event DBN8002 has good glufosinate herbicide tolerance and the yield is not compromised.

Example 8

Agricultural products or commodities can be produced from the transgenic soybean event DBN8002. If sufficient expression is detected in the agricultural products or commodities, they are expected to contain the nucleotide sequences that can be diagnostic for the presence of materials from the transgenic soybean event DBN8002 in the agricultural products or commodities. The agricultural products or commodities include, but are not limited to, soybean cakes, powders and oils, specifically lecithin, fatty acids, glycerol, sterols, edible oils, defatted soy flakes, defatted and baked soy flours, soy milk clots, bean curd, soy protein concentrates, isolated soy proteins, hydrolyzed vegetable proteins, organized soy proteins, soy protein fibers, and any other foods intended for consumption as a food source by an animal, etc. Probes or primer pairs-based nucleic acid detection methods and/or kits can be developed to detect the nucleotide sequences derived from the transgenic soybean event DBN8002 in a biological sample, such as those shown in SEQ ID NO: 1 or SEQ ID NO: 2, wherein the probe sequence or primer sequence is selected from the sequences as shown in SEQ ID NO: 1, SEQ ID NO: 2, SEQ ID NO: 3, SEQ ID NO: 4 and SEQ ID NO: 5 or portions thereof, so as to diagnose the presence of the transgenic soybean event DBN8002.

In conclusion, the transgenic soybean event DBN8002 of the present invention has good resistance against *Lepidoptera* insects and high tolerance to glufosinate herbicide without compromising the yield, and the detection methods of the present invention can accurately and rapidly identify whether a biological sample contains DNA molecules of the transgenic soybean event DBN8002.

The seeds corresponding to the transgenic soybean event DBN8002 were deposited under the Budapest Treaty at the General Microbiological Center of China Microbiological Culture Collection Management Committee (CGMCC for short, Address: No. 3, No. 1 Precinct, Beichen West Road, Chaoyang District, Beijing, Institute of Microbiology, Academy of Sciences of China, zip code 100101) on Feb. 19, 2019, of which the classification and nomenclature are soybean (*Glycine max*), the deposit status is viable, and the accession number is CGMCC No. 17299. The deposit will be deposited in the depository for 30 years.

At last, it should be noted that the above Examples are only used to illustrate the technical solutions of the present invention rather than limit the present invention. Although the present invention is described in detail with reference to the preferred Examples, those skilled in the art should understand that the technical solutions of the present invention could be modified or substituted equivalently without departing from the spirit and scope of the technical solutions of the present invention.

What is claimed is:

1. A nucleic acid sequence comprising SEQ ID NO: 1 or a complete complementary sequence thereof, wherein the nucleic acid sequence further comprises SEQ ID NO: 3 or a complete complementary sequence thereof, and/or SEQ ID NO: 5 or a complete complementary sequence thereof.

2. A DNA detection kit comprising at least one DNA molecule, wherein the DNA molecule comprises the nucleic acid sequence according to claim 1, and the DNA molecule acts as a DNA primer or a probe specific for the transgenic soybean event DBN8002 or progeny thereof.

3. The DNA detection kit according to claim 2, wherein the DNA molecule further comprises SEQ ID NO: 6 or a complete complementary sequence thereof, and/or SEQ ID NO: 7 or a complete complementary sequence thereof.

* * * * *

SEQUENCE LISTING

```
<160> NUMBER OF SEQ ID NOS: 31

<210> SEQ ID NO 1
<211> LENGTH: 22
<212> TYPE: DNA
<213> ORGANISM: Artificial Sequence
<220> FEATURE:
<223> OTHER INFORMATION: a sequence of 22 nucleotides in length that is
      located around the insertion junction at the 5' end of the
      inserted sequence in DBN8002

<400> SEQUENCE: 1
aaattaatta ctcaaacact ga                                              22

<210> SEQ ID NO 2
<211> LENGTH: 22
<212> TYPE: DNA
<213> ORGANISM: Artificial Sequence
<220> FEATURE:
<223> OTHER INFORMATION: a sequence of 22 nucleotides in length that is
      located around the insertion junction at the 3' end of the
      inserted sequence in DBN8002

<400> SEQUENCE: 2
ttacaccaca ataattatgt gt                                              22

<210> SEQ ID NO 3
<211> LENGTH: 1524
<212> TYPE: DNA
<213> ORGANISM: Artificial Sequence
<220> FEATURE:
<223> OTHER INFORMATION: a sequence of 1524 nucleotides that is located
      around the insertion junction at the 5' end of the inserted
      sequence in DBN8002

<400> SEQUENCE: 3
tccaaaccaa accgcatgtt aatttattgt ttggttcgaa tgtaattttg agaagaaaaa      60
aaattgctca aaccgcaccg cgaacaccct aatggtattg aagtgttttt ttttataaaa     120
aaattaacaa aaggaaaata atgataaatt taactttttt ttataaatgc acttcactt      180 ttaatttgga gaaattaaat gagaaaattg tataaaagtt gaagtgcata attatgtatt     240
ttttaatttt ttttttatct tcttttcttc tatgaatact taataagaaa cttgttcaaa     300
cataatgtat ataattttat gcatagaata acataattag agataaaagg aaattaattc     360
acaacagcta accaaagtcg tgttataatt cattaaccac ctaaatctat taaggtcgac     420
ctagtgatat aaaatatttg agtagtataa ggtctttggt tggattatcg gtaccaccat     480
tatatacaca taaaatcact aaccatacat gttggttaag taggttatga agtcttagat     540
aatgattgta aatcaaatga ctaattattt gagatctcat tttatgttag agtaagaatc     600
```
aatttttgtt taaaaaaaat atttagatac caaattaatt actcaaacac tgatagttta    660
aactgaaggc gggaaacgac aatctgatca tgagcggaga attaagggag tcacgttatg    720 accccccgccg atgacgcggg acaagccgtt ttacgtttgg aactgacaga accgcaacgc    780
tgcaggaatt ggccgcaggt ggatttgtat taaactaatg actaattagt ggcactagcc    840
tcaccgactt cgcagacgag gccgctaagt cgcagctacg ctctcaacgg cactgactag    900
gtagtttaaa cgtgcactta attaaggtac cgggaattta atcccggga ggtctcgcag    960 acctagctag ttagaatccc gagacctaag tgactagggt cacgtgaccc tagtcactta   1020
aagcttgtcg acaaaattta gaacgaactt aattatgatc tcaaatacat tgatacatat   1080
ctcatctaga tctaggttat cattatgtaa gaaagttttg acgaatatgg cacgacaaaa   1140
tggctagact cgatgtaatt ggtatctcaa ctcaacatta tacttatacc aaacattagt   1200
tagacaaaat ttaaacaact atttttttatg tatgcaagag tcagcatatg tataattgat   1260
tcagaatcgt tttgacgagt tcggatgtag tagtagccat tatttaatgt acatactaat   1320
cgtgaatagt gaatatgatg aaacattgta tcttattgta taaatatcca taaacacatc   1380
atgaaagaca ctttctttca cggtctgaat taattatgat acaattctaa tagaaaacga   1440
attaaattac gttgaattgt atgaaatcta attgaacaag ccaaccacga cgacgactaa   1500
cgttgcctgg attgactcgg ttta                                           1524

<210> SEQ ID NO 4
<211> LENGTH: 656
<212> TYPE: DNA
<213> ORGANISM: Artifical Sequence
<220> FEATURE:
<223> OTHER INFORMATION: a sequence of 656 nucleotides that is located
      around the insertion junction at the 3' end of the inserted
      sequence in DBN8002

<400> SEQUENCE: 4
gtgagtagtt cccagataag ggaattaggg ttcttatagg gtttcgctca tgtgttgagc     60
atataagaaa cccttagtat gtatttgtat ttgtaaaata cttctatcaa taaaattttct   120 aattcctaaa accaaaatcc agtggcctgc agggaattct taattaagtg cacgcggccg   180
cctacttagt caagagcctc gcacgcgact gtcacgcggc caggatcgcc tcgtgagcct   240
cgcaatctgt acctagttta gctagttagg acgttaacag gacgcgcct ggccgtatcc    300 gcaatgtgtt attaagttgt ctaagcgtca atttgtttac accacaataa ttatgtgtaa   360
cgcttgtttt gctatatatg ggacacttga ggaatgacat tattagttac gtaacttgca   420
ttaattaagt attcatgtgt ttgcataaaa aaatagtttt ctcatttcca tattagattt   480
tggaaaaaaa aaattcataa tcaaacttat acttttgttt atcctaaagc aaacacttcg   540
agagggttga attgtttctc atatgtgaag ttcattcaac cacgaatgtt tttttcgcaa   600
tatttacaag gtatgtctaa ttgatccgag taaaataagt tcaacagtct ctcttg        656

<210> SEQ ID NO 5
<211> LENGTH: 7344
<212> TYPE: DNA
<213> ORGANISM: Artifical sequence
<220> FEATURE:
<223> OTHER INFORMATION: the entire T-DNA sequence, 5' and 3' end
      soybean genomic flanking sequences

<400> SEQUENCE: 5
aaaaatccaa accaaaccgc atgttaattt attgtttggt tcgaatgtaa ttttgagaag     60

-continued

```
aaaaaaaatt gctcaaaccg caccgcgaac accctaatgg tattgaagtg tttttttta      120 taaaaaaatt aacaaaagga aataatgat aaatttaact ttttttata aatgcacttc       180 acttttaat ttggagaaat taaatgagaa aattgtataa aagttgaagt gcataattat      240 gtattttta attttttttt tatcttcttt tcttctatga atacttaata agaaacttgt      300
tcaaacataa tgtatataat tttatgcata gaataacata attagagata aaggaaatt     360 aattcacaac agctaaccaa agtcgtgtta taattcatta accacctaaa tctattaagg    420
tcgacctagt gatataaaat atttgagtag tataaggtct ttggttggat tatcggtacc    480
accattatat acacataaaa tcactaacca tacatgttgg ttaagtaggt tatgaagtct    540
tagataatga ttgtaaatca aatgactaat tatttgagat ctcattttat gttagagtaa   600
gaatcaattt ttgtttaaaa aaaatattta gataccaaat taattactca aacactgata   660
gtttaaactg aaggcgggaa acgacaatct gatcatgagc ggagaattaa gggagtcacg   720
ttatgacccc cgccgatgac gcgggacaag ccgttttacg tttggaactg acagaaccgc   780
aacgctgcag gaattggccg caggtggatt tgtattaaac taatgactaa ttagtggcac   840
tagcctcacc gacttcgcag acgaggccgc taagtcgcag ctacgctctc aacggcactg   900
actaggtagt ttaaacgtgc acttaattaa ggtaccggga atttaaatcc cgggaggtct   960
cgcagaccta gctagttaga atcccgagac ctaagtgact agggtcacgt gaccctagtc  1020
acttaaagct tgtcgacaaa atttagaacg aacttaatta tgatctcaaa tacattgata  1080
catatctcat ctagatctag gttatcatta tgtaagaaag ttttgacgaa tatggcacga  1140
caaaatggct agactcgatg taattggtat ctcaactcaa cattatactt ataccaaaca  1200
ttagttagac aaaattttaaa caactatttt ttatgtatgc aagagtcagc atatgtataa  1260
ttgattcaga atcgttttga cgagttcgga tgtagtagta gccattattt aatgtacata  1320
ctaatcgtga atagtgaata tgatgaaaca ttgtatctta ttgtataaat atccataaac  1380
acatcatgaa agacactttc tttcacggtc tgaattaatt atgatacaat tctaatagaa  1440
aacgaattaa attacgttga attgtatgaa atctaattga acaagccaac cacgacgacg  1500
actaacgttg cctggattga ctcggtttaa gttaaccact aaaaaaacgg agctgtcatg  1560
taacacgcgg atcgagcagg tcacagtcat gaagccatca agcaaaaga actaatccaa   1620 gggctgagat gattaattag tttaaaaatt agttaacacg agggaaaagg ctgtctgaca  1680
gccaggtcac gttatctta cctgtggtcg aaatgattcg tgtctgtcga ttttaattat   1740 tttttgaaa ggccgaaaat aaagttgtaa gagataaacc cgcctatata aattcatata  1800
ttttcctctc cgctttgaat tgtctcgttg tcctcctcac tttcatcagc cgttttgaat  1860
ctccggcgac ttgacagaga agaacaagga agaagactaa gagagaaagt aagagataat  1920
ccaggagatt cattctccgt tttgaatctt cctcaatctc atcttcttcc gctctttctt   1980
tccaaggtaa taggaacttt ctggatctac tttatttgct ggatctcgat cttgttttct   2040
caatttcctt gagatctgga attcgtttaa tttggatctg tgaacctcca ctaaatcttt  2100
tggttttact agaatcgatc taagttgacc gatcagttag ctcgattata gctaccagaa  2160
tttggcttga ccttgatgga gagatccatg ttcatgttac ctgggaaatg atttgtatat  2220
gtgaattgaa atctgaactg ttgaagttag attgaatctg aacactgtca atgttagatt  2280
gaatctgaac actgtttaag gttagatgaa gtttgtgtat agattcttcg aaactttagg  2340
atttgtagtg tcgtacgttg aacagaaagc tatttctgat tcaatcaggg tttatttgac  2400
```

```
tgtattgaac tctttttgtg tgtttgcagc tcataaaaag agctcatgaa caagaacaac    2460
accaagctct ccacacgggc acttccctcc tttattgact actttaatgg catctatggg    2520
tttgctacgg ggatcaagga cattatgaac atgatcttca agacagacac tggcggggat    2580
cttacgctcg acgagattct taagaatcag caactcctga cgatatctc tggcaagctg     2640 gacggcgtga atgggtcact taacgacctc atcgctcagg ggaatctcaa cacagaactg    2700
tctaaggaga tcctcaagat tgcaaatgag cagaaccaag ttcttaatga tgtgaacaat    2760
aagctcgacg ccatcaacac aatgcttcgc gtgtacctcc caaagattac tagcatgctc    2820
tcggacgtca tgaagcagaa ctacgcgctg tcccttcaaa ttgagtatct gagcaagcag    2880
cttcaagaaa tctcggacaa gctggatatc attaatgtga acgtcctcat caacagcacc    2940
ctgacggaga ttacaccggc gtaccagagg atcaagtatg tgaatgagaa gttcgaggaa    3000 ctcactttg ctacagaaac ttccagcaag gtcaagaagg atggctcacc agccgacatc     3060
ctggatgagc ttacagaact cactgagctg gcgaagtccg tgaccaagaa tgacgtcgat    3120
ggcttcgagt tttacctgaa cacgttccac gacgttatgg tgggcaacaa tcttttggg     3180 cggagcgctc tcaagactgc atcggaactg atcaccaagg agaacgttaa gacgagcggc    3240
tcggaggtcg ggaatgttta caacttcctt atcgtcctca ccgcactcca ggcccaagcg    3300
tttctcacgc tgaccacctg ccgcaagctc ctcggcctcg cagacatcga ttacacctcc    3360
atcatgaacg agcacctgaa caaggagaag gaggagttcc gcgtgaatat ccttccgaca    3420
ctctcgaaca ctttttctaa tccaaactac gctaaggtca agggctccga cgaagatgca    3480
aagatgatcg ttgaggccaa gcctggccat gcgctcatcg ggttcgagat ttctaacgac    3540
tcaattaccg tgctgaaggt ctacgaggcg aagctcaagc agaattatca agtggacaag    3600
gattctctgt cagaggttat ctacggcgac atggataagc tgctttgccc tgatcagtcc    3660
gagcaaatct actatacgaa caatattgtc ttccccaacg aatacgtgat caccaagatt    3720
gactttacga agaagatgaa gacactccgg tacgaggtga cggctaactt ctatgattcg    3780
tctacgggcg agatcgacct caacaagaag aaggtcgaat catccgaggc cgaatacaga    3840
accctgtcgg cgaacgacga tggcgtgtat atgcctcttg gggtcatttc tgagaccttc    3900
ctcacgccca tcaatggctt tgggctccag gcagatgaga actcccgcct gatcacccttt   3960 acgtgcaaga gctacctcag ggagctgctg cttgccaccg acctctctaa caaggaaacg    4020
aagctgatcg ttccgccatc aggcttcatc tccaatattg tggagaacgg gtcaattgag    4080
gaagataatc tggaaccgtg gaaggctaac aataagaacg catacgttga ccacacaggc    4140
ggggtgaatg gcactaaggc gctctatgtg cataaggatg gtggcatctc ccagttcatt    4200
ggcgacaagc tgaagccgaa gacagaatac gtgattcaat atactgtgaa gggcaagcca    4260
agcatccacc tcaaggatga gaacacaggg tacatccatt acgaagatac taacaacaac    4320
ctggaggact accagacaat caataagagg ttcacaactg gcactgacct gaaggggtc    4380 tatcttattc tcaagtccca gaatggcgat gaggcctggg gcgacaactt catcattctc    4440
gaaatctccc ctagcgagaa gctcctgagc cccgagctga ttaacaccaa taactggaca    4500
tccactggca gcacgaatat ctcggggaac accctgacgc tttaccaggg cgggagaggc    4560
attctgaagc agaacctcca actggattcg ttctctacct acagagtcta ttttcagtt    4620 tccggcgacg cgaatgtgcg catcaggaac tcgcgggaag tcctcttcga gaagagatac    4680
atgtctggcg ctaaggatgt gtcagaaatg ttcaccacga gtttgagaa ggacaacttt    4740 tatatcgaac tgtcccaagg gaataacctc tacggcggcc ccattgttca tttttacgac    4800
```

```
gtgagcatca agtgaggcgc cgatcgttca acatttggc aataaagttt cttaagattg    4860
aatcctgttg ccggtcttgc gatgattatc atataatttc tgttgaatta cgttaagcat    4920
gtaataatta acatgtaatg catgacgtta tttatgagat gggtttttat gattagagtc    4980
ccgcaattat acatttaata cgcgatagaa acaaaatat agcgcgcaaa ctaggataaa    5040
ttatcgcgcg cggtgtcatc tatgttacta gatcggcgcg ccagtaagtg actagagtca    5100
cgtgacccta gtcacttaaa tcctaggcca tggagtcaaa gattcaaata gaggacctaa    5160
cagaactcgc cgtaaagact ggcgaacagt tcatacagag tctcttacga ctcaatgaca    5220
agaagaaaat cttcgtcaac atggtggagc acgacacgct tgtctactcc aaaaatatca    5280
aagatacagt ctcagaagac caaagggcaa ttgagacttt tcaacaaagg gtaatatccg    5340
gaaacctcct cggattccat tgcccagcta tctgtcactt tattgtgaag atagtggaaa    5400
aggaaggtgg ctcctacaaa tgccatcatt gcgataaagg aaaggccatc gttgaagatg    5460
cctctgccga cagtggtccc aaagatggac ccccacccac gaggagcatc gtggaaaaag    5520
aagacgttcc aaccacgtct tcaaagcaag tggattgatg tgatatctcc actgacgtaa    5580
gggatgacgc acaatcccac tatccttcgc aagacccttc ctctatataa ggaagttcat    5640
ttcatttgga gaggacaggg tacccgggga tccaccatgt ctccggagag gagaccagtt    5700
gagattaggc cagctacagc agctgatatg ccgcggttt tgatatcgt taaccattac    5760
attgagacgt ctacagtgaa ctttaggaca gagccacaaa caccacaaga gtggattgat    5820
gatctagaga ggttgcaaga tagatacct tggttggttg ctgaggttga gggtgttgtg    5880
gctggtattg cttacgctgg gccctggaag gctaggaacg cttacgattg gacagttgag    5940
agtactgttt acgtgtcaca taggcatcaa aggttgggcc taggatccac attgtacaca    6000
catttgctta agtctatgga ggcgcaaggt tttaagtctg tggttgctgt tataggcctt    6060
ccaaacgatc catctgttag gttgcatgag gctttgggat acacagcccg gggtacattg    6120
cgcgcagctg gatacaagca tggtggatgg catgatgttg gtttttggca aagggatttt    6180
gagttgccag ctcctccaag gccagttagg ccagttaccc agatctgagt cgacctgcag    6240
gcatgcccgc tgaaatcacc agtctctctc tacaaatcta tctctctcta taataatgtg    6300
tgagtagttc ccagataagg gaattagggt tcttataggg tttcgctcat gtgttgagca    6360
tataagaaac ccttagtatg tatttgtatt tgtaaaatac ttctatcaat aaaatttcta    6420
attcctaaaa ccaaaatcca gtggcctgca gggaattctt aattaagtgc acgcggccgc    6480
ctacttagtc aagagcctcg cacgcgactg tcacgcggcc aggatcgcct cgtgagcctc    6540
gcaatctgta cctagtttag ctagttagga cgttaacagg gacgcgcctg ccgtatccg    6600
caatgtgtta ttaagttgtc taagcgtcaa tttgtttaca ccacaataat tatgtgtaac    6660
gcttgttttg ctatatatgg gacacttgag gaatgacatt attagttacg taacttgcat    6720
taattaagta ttcatgtgtt tgcataaaaa aatagttttc tcatttccat attagatttt    6780
ggaaaaaaaa aattcataat caaacttata cttttgttta tcctaaagca aacacttcga    6840
gagggttgaa ttgtttctca tatgtgaagt tcattcaacc acgaatgttt ttttcgcaat    6900
atttacaagg tatgtctaat tgatccgagt aaaataagtt caacagtctc tcttgaataa    6960
tcaatagaaa ttttttaaaca attatcttat tttcaattca attattaatg ttatgactat    7020
tacatttaat atttttatctt taatttctct ttcatatcat ttatgtataa aattaaaact    7080
ttataattat taattaaaag ttaataatta aactatact aaaatgcata aatatatata    7140
```

-continued

```
ataaaattat aaaatattaa aatcttaata attattttt caatcattat attatttatt    7200
cacgttagga aaaatatata tgctgtaatt ttaatttta tatttttat ctataacttt      7260 taattaaaat ttatactttt atctataatt tttaattaaa atataatgaa aatgttggaa    7320
aagtaaagta ttatacttag gagt                                          7344
```

<210> SEQ ID NO 6
<211> LENGTH: 219
<212> TYPE: DNA
<213> ORGANISM: Artificial Sequence
<220> FEATURE:
<223> OTHER INFORMATION: a sequence located in SEQ ID NO: 3, spanning
      the DNA sequence of the pDBN4006 construct and a prAtAct2
      transcription origin sequence

<400> SEQUENCE: 6

```
cgtgcactta attaaggtac cgggaattta atcccggga ggtctcgcag acctagctag     60
ttagaatccc gagacctaag tgactagggt cacgtgaccc tagtcactta aagcttgtcg   120
acaaaattta gaacgaactt aattatgatc tcaaatacat tgatacatat ctcatctaga   180
tctaggttat cattatgtaa gaaagttttg acgaatatg                          219
```

<210> SEQ ID NO 7
<211> LENGTH: 243
<212> TYPE: DNA
<213> ORGANISM: Artificial Sequence
<220> FEATURE:
<223> OTHER INFORMATION: a sequence located in SEQ ID NO: 4, spanning a
      t35S transcriptional terminator sequence and the DNA sequence of
      the pDBN4006 construct

<400> SEQUENCE: 7

```
gtgagtagtt cccagataag ggaattaggg ttcttatagg gtttcgctca tgtgttgagc     60
atataagaaa cccttagtat gtatttgtat ttgtaaaata cttctatcaa taaaatttct   120
aattcctaaa accaaaatcc agtggcctgc agggaattct taattaagtg cacgcggccg   180
cctacttagt caagagcctc gcacgcgact gtcacgcggc caggatcgcc tcgtgagcct   240
cgc                                                                243
```

<210> SEQ ID NO 8
<211> LENGTH: 20
<212> TYPE: DNA
<213> ORGANISM: Artificial Sequence
<220> FEATURE:
<223> OTHER INFORMATION: a first primer for amplifying SEQ ID NO: 3

<400> SEQUENCE: 8

```
tccaaaccaa accgcatgtt                                                20
```

<210> SEQ ID NO 9
<211> LENGTH: 19
<212> TYPE: DNA
<213> ORGANISM: Artificial Sequence
<220> FEATURE:
<223> OTHER INFORMATION: a second primer for amplifying SEQ ID NO: 3

<400> SEQUENCE: 9

```
taaaccgagt caatccagg                                                 19
```

<210> SEQ ID NO 10
<211> LENGTH: 20
<212> TYPE: DNA
<213> ORGANISM: Artificial Sequence

```
<220> FEATURE:
<223> OTHER INFORMATION: a first primer for amplifying SEQ ID NO: 4

<400> SEQUENCE: 10
gtgagtagtt cccagataag                                              20

<210> SEQ ID NO 11
<211> LENGTH: 20
<212> TYPE: DNA
<213> ORGANISM: Artificial Sequence
<220> FEATURE:
<223> OTHER INFORMATION: a second primer for amplifying SEQ ID NO: 4

<400> SEQUENCE: 11
caagagagac tgttgaactt                                              20

<210> SEQ ID NO 12
<211> LENGTH: 26
<212> TYPE: DNA
<213> ORGANISM: Artificial Sequence
<220> FEATURE:
<223> OTHER INFORMATION: a primer from 5' flanking genomic sequence

<400> SEQUENCE: 12
gagatctcat tttatgttag agtaag                                       26

<210> SEQ ID NO 13
<211> LENGTH: 24
<212> TYPE: DNA
<213> ORGANISM: Artificial Sequence
<220> FEATURE:
<223> OTHER INFORMATION: a primer from T-DNA, which is paired with SEQ
      ID NO: 12

<400> SEQUENCE: 13
ctacctagtc agtgccgttg agag                                         24

<210> SEQ ID NO 14
<211> LENGTH: 21
<212> TYPE: DNA
<213> ORGANISM: Artificial Sequence
<220> FEATURE:
<223> OTHER INFORMATION: a primer from 3' flanking genomic sequence,
      which can be used in pair with SEQ ID NO: 12 to detect whether a
      transgene is homozygous or heterozygous

<400> SEQUENCE: 14
agaaacaatt caaccctctc g                                            21

<210> SEQ ID NO 15
<211> LENGTH: 21
<212> TYPE: DNA
<213> ORGANISM: Artificial Sequence
<220> FEATURE:
<223> OTHER INFORMATION: a primer from T-DNA, which is paired with SEQ
      ID NO: 14

<400> SEQUENCE: 15
cctaaaacca aaatccagtg g                                            21

<210> SEQ ID NO 16
<211> LENGTH: 21
<212> TYPE: DNA
<213> ORGANISM: Artificial Sequence
<220> FEATURE:
<223> OTHER INFORMATION: a first primer for detecting mVip3Aa gene in
      Taqman
```

<400> SEQUENCE: 16
cgaatacaga accctgtcgg c                                          21

<210> SEQ ID NO 17
<211> LENGTH: 24
<212> TYPE: DNA
<213> ORGANISM: Artificial Sequence
<220> FEATURE:
<223> OTHER INFORMATION: a second primer for detecting mVip3Aa gene in
      Taqman

<400> SEQUENCE: 17
cgtgaggaag gtctcagaaa tgac                                       24

<210> SEQ ID NO 18
<211> LENGTH: 27
<212> TYPE: DNA
<213> ORGANISM: Artificial Sequence
<220> FEATURE:
<223> OTHER INFORMATION: a probe for detecting mVip3Aa gene in Taqman

<400> SEQUENCE: 18
cgacgatggc gtgtatatgc ctcttgg                                    27

<210> SEQ ID NO 19
<211> LENGTH: 22
<212> TYPE: DNA
<213> ORGANISM: Artificial Sequence
<220> FEATURE:
<223> OTHER INFORMATION: a first primer for detecting PAT gene in Taqman

<400> SEQUENCE: 19
gagggtgttg tggctggtat tg                                         22

<210> SEQ ID NO 20
<211> LENGTH: 23
<212> TYPE: DNA
<213> ORGANISM: Artificial Sequence
<220> FEATURE:
<223> OTHER INFORMATION: a second primer for detecting PAT gene in
      Taqman

<400> SEQUENCE: 20
tctcaactgt ccaatcgtaa gcg                                        23

<210> SEQ ID NO 21
<211> LENGTH: 25
<212> TYPE: DNA
<213> ORGANISM: Artificial Sequence
<220> FEATURE:
<223> OTHER INFORMATION: a probe for detecting PAT gene in Taqman

<400> SEQUENCE: 21
cttacgctgg gccctggaag gctag                                      25

<210> SEQ ID NO 22
<211> LENGTH: 25
<212> TYPE: DNA
<213> ORGANISM: Artificial Sequence
<220> FEATURE:
<223> OTHER INFORMATION: a first primer for soybean endogenous gene
      lectin

<400> SEQUENCE: 22
tgccgaagca accaaacatg atcct                                      25

<210> SEQ ID NO 23
<211> LENGTH: 25
<212> TYPE: DNA
<213> ORGANISM: Artificial Sequence
<220> FEATURE:
<223> OTHER INFORMATION: a second primer for soybean endogenous gene
      lectin

<400> SEQUENCE: 23
tgatggatct gatagsattg acgtt                                          25

<210> SEQ ID NO 24
<211> LENGTH: 346
<212> TYPE: DNA
<213> ORGANISM: Artificial Sequence
<220> FEATURE:
<223> OTHER INFORMATION: a probe for mVip3Aa gene in Southern blot assay

<400> SEQUENCE: 24
acagaactca ctgagctggc gaagtccgtg accaagaatg acgtcgatgg cttcgagttt    60
tacctgaaca cgttccacga cgttatggtg ggcaacaatc tttttgggcg gagcgctctc   120
aagactgcat cggaactgat caccaaggag aacgttaaga cgagcggctc ggaggtcggg   180
aatgtttaca acttccttat cgtcctcacc gcactccagg cccaagcgtt tctcacgctg   240
accacctgcc gcaagctcct cggcctcgca gacatcgatt acacctccat catgaacgag   300
cacctgaaca aggagaagga ggagttccgc gtgaatatcc ttccga                  346

<210> SEQ ID NO 25
<211> LENGTH: 310
<212> TYPE: DNA
<213> ORGANISM: Artificial Sequence
<220> FEATURE:
<223> OTHER INFORMATION: a probe for PAT gene in Southern blot assay

<400> SEQUENCE: 25
cagacttaaa accttgcgcc tccatagact taagcaaatg tgtgtacaat gtggatccta    60
ggcccaacct tgatgccta tgtgacacgt aaacagtact ctcaactgtc caatcgtaag   120
cgttcctagc cttccagggc ccagcgtaag caataccagc cacaacaccc tcaacctcag   180
caaccaacca agggtatcta tcttgcaacc tctctagatc atcaatccac tcttgtggtg   240
tttgtggctc tgtcctaaag ttcactgtag acgtctcaat gtaatggtta acgatatcac   300
aaaccgcggc                                                          310

<210> SEQ ID NO 26
<211> LENGTH: 20
<212> TYPE: DNA
<213> ORGANISM: Artificial Sequence
<220> FEATURE:
<223> OTHER INFORMATION: a primer from T-DNA, which has the same
      direction as SEQ ID NO: 13

<400> SEQUENCE: 26
cgtgacccta gtcacttagg                                                20

<210> SEQ ID NO 27
<211> LENGTH: 23
<212> TYPE: DNA
<213> ORGANISM: Artificial Sequence
<220> FEATURE:
<223> OTHER INFORMATION: a primer from T-DNA, which has an opposite
      direction to SEQ ID NO: 13 and is used for obtaining a flanking -continued

```
     sequence

<400> SEQUENCE: 27
ctgtggtcga aatgattcgt gtc                                            23

<210> SEQ ID NO 28
<211> LENGTH: 19
<212> TYPE: DNA
<213> ORGANISM: Artificial sequence
<220> FEATURE:
<223> OTHER INFORMATION: a primer from T-DNA, which has an opposite
      direction to SEQ ID NO: 13 and is used for obtaining a flanking
      sequence

<400> SEQUENCE: 28
cgctctttct ttccaaggt                                                 19

<210> SEQ ID NO 29
<211> LENGTH: 20
<212> TYPE: DNA
<213> ORGANISM: Artificial Sequence
<220> FEATURE:
<223> OTHER INFORMATION: a primer from T-DNA, which has the same
      direction as SEQ ID NO: 15

<400> SEQUENCE: 29
ttaggccagt tacccagatc                                                20

<210> SEQ ID NO 30
<211> LENGTH: 22
<212> TYPE: DNA
<213> ORGANISM: Artificial Sequence
<220> FEATURE:
<223> OTHER INFORMATION: a primer from T-DNA, which has an opposite
      direction to SEQ ID NO: 15 and is used for obtaining a flanking
      sequence

<400> SEQUENCE: 30
aaccttgcgc ctccatagac tt                                             22

<210> SEQ ID NO 31
<211> LENGTH: 20
<212> TYPE: DNA
<213> ORGANISM: Artificial Sequence
<220> FEATURE:
<223> OTHER INFORMATION: a primer from T-DNA, which has an opposite
      direction to SEQ ID NO: 15 and is used for obtaining a flanking
      sequence

<400> SEQUENCE: 31
ccagccacaa caccctcaac                                                20
```